(12) United States Patent
Tabernero et al.

(10) Patent No.: US 8,801,781 B2
(45) Date of Patent: Aug. 12, 2014

(54) INTRAOCULAR LENS FOR CORRECTING CORNEAL COMA

(75) Inventors: Juan Tabernero, Murcia (ES); Pablo Artal, Murcia (ES); Patricia Piers, Groningen (NL)

(73) Assignee: Abbott Medical Optics Inc., Santa Ana, CA (US)

( * ) Notice: Subject to any disclaimer, the term of this patent is extended or adjusted under 35 U.S.C. 154(b) by 1675 days.

(21) Appl. No.: 11/260,013

(22) Filed: Oct. 26, 2005

(65) Prior Publication Data

US 2007/0093891 A1    Apr. 26, 2007

(51) Int. Cl.
*A61F 2/16* (2006.01)
*A61B 3/00* (2006.01)

(52) U.S. Cl.
CPC ............. *A61B 3/0025* (2013.01); *A61F 2/1613* (2013.01)
USPC ........................................ 623/6.23; 623/6.11

(58) Field of Classification Search
USPC ....................................................... 623/6.11
See application file for complete search history.

(56) References Cited

U.S. PATENT DOCUMENTS

| | | | |
|---|---|---|---|
| 5,019,098 A | 5/1991 | Mercier | |
| 5,050,981 A | 9/1991 | Roffman | |
| 5,236,970 A | 8/1993 | Christ et al. | |
| 5,282,852 A | 2/1994 | Capetan et al. | |
| 5,444,106 A | 8/1995 | Zhou et al. | |
| 5,489,302 A * | 2/1996 | Skottun | 623/6.13 |
| 5,760,871 A | 6/1998 | Kosoburd et al. | |
| 5,777,719 A | 7/1998 | Williams et al. | |
| 5,968,095 A | 10/1999 | Norrby | |
| 6,007,747 A | 12/1999 | Blake et al. | |
| 6,050,687 A | 4/2000 | Bille et al. | |
| 6,095,651 A | 8/2000 | Williams et al. | |

(Continued)

FOREIGN PATENT DOCUMENTS

EP  1262815 A2  12/2002
EP  1424049 A1  6/2004

(Continued)

OTHER PUBLICATIONS

Artal et al. (Nov. 1, 1998). Contributions of the cornea and the lens to the aberrations of the human eye. *Optics Letters*, vol. 23, No. 21, pp. 1713-1715.

(Continued)

*Primary Examiner* — Bruce E Snow
*Assistant Examiner* — Melissa Hoban
(74) *Attorney, Agent, or Firm* — Abbott Medical Optics Inc.

(57) ABSTRACT

When fitting a patient for an intraocular lens, a series of measurements is taken on the patient's eye that determines a required lens power. Next, a range of preferred shape factors may be found, which determine the base (i.e., spherical) radii of the two lens surfaces, essentially independent of the lens power. The preferred shape factor adjusts the third-order coma of the lens to largely offset the coma of the cornea, so that the image at the retina has a reduced amount of third-order coma. Once a preferred shape factor is determined, the base radii of curvature of the anterior and posterior surfaces are determined from the shape factor and the lens power by algebraic formulas. Finally, one or more aspheric terms are added to one or both of the surfaces in the lens, so that the spherical aberration of the lens largely offsets the spherical aberration of the cornea.

21 Claims, 15 Drawing Sheets

(56) References Cited

U.S. PATENT DOCUMENTS

| | | | |
|---|---|---|---|
| 6,224,211 B1 | 5/2001 | Gordon | |
| 6,413,276 B1 | 7/2002 | Werblin | |
| 6,609,793 B2 | 8/2003 | Norrby et al. | |
| 7,036,931 B2* | 5/2006 | Lindacher et al. | 351/161 |
| 7,137,702 B2* | 11/2006 | Piers et al. | 351/177 |
| 2003/0081171 A1* | 5/2003 | Griffin | 351/161 |
| 2003/0151721 A1 | 8/2003 | Lai et al. | |
| 2004/0148022 A1* | 7/2004 | Eggleston | 623/6.22 |
| 2004/0156014 A1* | 8/2004 | Piers et al. | 351/168 |
| 2005/0043794 A1* | 2/2005 | Geraghty et al. | 623/6.23 |
| 2005/0192667 A1* | 9/2005 | Schachar | 623/6.11 |
| 2005/0203619 A1* | 9/2005 | Altmann | 623/6.23 |

FOREIGN PATENT DOCUMENTS

| | | |
|---|---|---|
| WO | WO 9831299 | 7/1998 |
| WO | WO0075716 A1 | 12/2000 |
| WO | WO02088830 A1 | 11/2002 |

OTHER PUBLICATIONS

Atchison. (Apr. 1991). Design of aspheric intraocular lens. *Ophthal. Physiol. Opt.* vol. 11, pp. 137-146.

Glasser et al. (1998). Presbyopia and the optical changes in the human crystalline lens with age. *Vision Res.*, vol. 38, No. 2, pp. 209-299.

Greivenkamp et al. (1995). Visual acuity modeling using optical raytracing of schematic eyes. *American Journal of Ophthalmology.* 120:227-240.

Guirao. (Jun. 2000). Corneal wave aberration from videokeratography: accuracy and limitations of the procedure. *Journal of the Optical Society of America*, vol. 17, No. 6, pp. 955-965.

Liang et al. (1994). Objective measurement of wave aberrations of the human eye with the use of a Hartmann-Shack wave-front sensor. *Journal of the Optical Society of America*, vol. 11, No. 7, pp. 1949-1957.

Malacara et al. (Jun. 1990). Wavefront fitting with discrete orthogonal polynomials in a unit radius circle. *Optical Engineering*, vol. 29, No. 6, pp. 672-675.

Oshika et al. (Jun. 1999). Changes in Corneal Wavefront Aberrations with Aging. *Investigative Ophthalmology & Visual Science.*—vol. 40, No. 7, pp. 1351-1354.

Patel et al. (May/Jun. 1993). Shape and radius of posterior corneal surface. *Refractive and Corneal Surgery.* vol. 9, pp. 173-181.

Rowsey et al. (Sep.-Oct. 1998). Surgical correction of moderate myopia: which method should youchoose? *Survey of Ophthalmology*, vol. 43, No. 2, pp. 147-156.

Schwiegerling. Oct. 1995). Representation of videokeratoscopic height data with Zernike polynomials. *Journal of the Optical Society of America*, vol. 12, No. 10, pp. 2105-2113.

Smith et al. (2001). The spherical aberration of the crystalline lens of the human eye. *Vision Research*. 41:235-243.

Wang et al. (May 1, 1980). Wave-front interpretation with Zernike polynomials. *Applied Optics*, vol. 19, No. 9, pp. 1510-1518.

IOVS, Mar. 15, 1999, vol. 40, No. 4; S535.

IOVS, Mar. 15, 1999, vol. 40, No. 4; S545.

* cited by examiner

| | Axial Length [mm] | 23.5 | | | | | | |
|---|---|---|---|---|---|---|---|---|
| | Effective Lens Position [mm] | 5.25 | | | | | | |
| | | Spectacle | Cornea | Aperture Stop | Anterior Lens | Posterior Lens | Retina | Total |
| | Radius, R [mm] | | 7.5 | 1E+99 | 110.23863 | -5.852288 | | |
| | Curvature, c [mm-1] | | 0.1333333 | 1E-99 | 0.0090712 | -0.170873 | | |
| | Thickness before surface, t [mm] | | 14 | 3.74 | 1.51 | 1.1 | 17.15 | |
| | Thickness after surface, t' [mm] | 14 | 3.74 | 1.51 | 1.1 | 17.15 | | |
| | Refractive index before surface, n | 1 | 1 | 1.336 | 1.336 | 1.4577 | 1.336 | |
| | Refractive index after surface, n' | 1 | 1.336 | 1.336 | 1.4577 | 1.336 | | |
| | Power, phi [mm-1] | -0.0005 | 0.0448 | 0 | 0.001104 | 0.0207953 | | |
| | Power, phi [Diopters] | -0.5 | 44.8 | 0 | 1.1039687 | 20.795286 | | |
| | Marginal ray | | | | | | | |
| | Ray height, y [mm] | 3 | 3.021 | 2.6463259 | 2.4950537 | 2.3919771 | 0 | |
| | Ray angle before surface, u [radians] | 0 | 0.0015 | -0.10018 | -0.10018 | -0.093706 | -0.139474 | |
| | Ray angle after surface, u' [radians] | 0.0015 | -0.10018 | -0.10018 | -0.093706 | -0.139474 | | |
| | Chief ray | | | | | | | |
| | Ray height, ybar [mm] | -1.492045 | -0.277648 | 0 | 0.1120986 | 0.1868487 | 1.4085545 | |
| | Ray angle before surface, ubar [radians] | 0.0874887 | 0.0867426 | 0.0742375 | 0.0742375 | 0.0679547 | 0.0712365 | |
| | Ray angle after surface, ubar' [radians] | 0.0867426 | 0.0742375 | 0.0742375 | 0.0679547 | 0.0712365 | | |
| | Paraxial constants of eye system | | | | | | | |
| | Effective focal length [mm] | | | | | | | 21.509403 |
| | Numerical aperture | | | | | | | 0.1857336 |
| | Field of view [degrees] | | | | | | | 4.9999997 |
| | Lagrange invariant [mm] | 0.262466 | 0.262466 | 0.262466 | 0.262466 | 0.262466 | 0.262466 | |
| | Aberrations | | | | | | | |
| | Wavelength [nm] | | | | | | | 555 |
| | "A" = ni = nu + nyC | | 0.4043 | -0.133841 | -0.103603 | -0.732394 | | |
| | "B" = nibar = nubar + nybarC | | 0.0497229 | 0.0991813 | 0.1005398 | 0.0525169 | | |
| | W131 contribution [waves] | | 4.1847085 | 0 | 0.2505653 | -3.32479 | | 1.1104841 |
| IOL properties, calculated from: | | Ray trace | Thin-lens formula (t=0) | | | | | |
| Power of IOL [D] | | 21.881931 | 19.563028 | | | | | |
| Conjugate factor, Y | | 6.0990555 | 6.4840644 | | | | | |
| Shape factor, X | | -0.899178 | | | | | | |

Fig. 14

INTRAOCULAR LENS FOR CORRECTING CORNEAL COMA

BACKGROUND OF THE INVENTION

1. Field of the Invention

The present invention is directed to an intraocular lens, and more particularly to an intraocular lens that corrects for the coma of the cornea.

2. Background

To aid in understanding this invention, a background of some basic optics fundamentals is provided below.

FIG. 1 shows a cross-section of a human eye 10. Under normal conditions, light rays 11 originating from an object 12 enter the eye 10 through the cornea 13, pass through a liquid known as the aqueous humor 14, pass through the iris 15, pass through the lens 16, pass through another liquid known as the vitreous humor 17, and form an image 18 on the retina 19.

The eye can suffer diseases that impair a patient's vision. For instance, a cataract may increase the opacity of the lens 16, causing blindness. To restore the patient's vision, the diseased lens may be surgically removed and replaced with an artificial lens, known as an intraocular lens, or IOL. A patient whose natural lens has been removed is said to have aphakia, and one who surgically receives an artificial lens is said to have pseudophakic vision.

In the absence of aberrations and diffraction, there is an essentially one-to-one correspondence between points on the object 12 and points on the image 18. FIGS. 2 and 3 show an example of aberration-free imaging, using a generic lens 21. The generic lens 21 is drawn as a simple two-surface lens, but is intended to represent the chain of optical elements in the eye, including the cornea 13 and the lens 16. An object 23 forms an image 24 on the retina 22. An on-axis bundle of rays 29 originating at the base 25 of the object 23 passes through the generic lens 21, and the rays strike the retina 22 at the base 27 of the image 24. Similarly, an off-axis bundle of rays 31 originating at the edge 26 of the object 23 passes through the generic lens 21, and the rays strike the retina 22 at the edge 28 of the image 24. In general, the visual acuity of the eye is directly related to the amount of aberration present in the eye's optical system, and any reduction in aberration is desirable.

An intraocular lens is typically corrected for a single focus, meaning that objects at a particular position away from the eye appear in focus, while objects at an increasing distance away from that position appear increasingly blurred.

This is illustrated in FIGS. 4 through 7. In FIGS. 4 and 5, a too-distant object 43, more distant from the generic lens 21 than object 23, forms an image 44 that is axially translated away from the retina 22 toward the lens 21. FIG. 4 shows an on-axis bundle of rays, and FIG. 5 shows an off-axis bundle of rays. In terms of aberrations, the optical system 40 in FIGS. 4 and 5 shows a positive amount of defocus.

A positive amount of defocus can occur even if the eye has its natural lens 16, if the range over which the natural lens 16 can accommodate is too small. When occurring with the natural lens 16, this condition is known medically as myopia, or nearsightedness, and can be remedied by spectacles or a contact lens that introduces negative optical power into the eye's optical system, thereby increasing the effective focal length of the system and axially translating the image 44 back toward the retina 22.

Similarly, in FIGS. 6 and 7, a too-close object 63, closer to the generic lens 21 than object 23, forms an image 64 that is axially translated away from the retina 22 away from the lens 21. Although the rays are drawn in FIGS. 6 and 7 as propagating beyond the retina to the image 64, in reality, the rays terminate at the retina 22 before forming an image. FIG. 6 shows an on-axis bundle of rays, and FIG. 7 shows an off-axis bundle of rays. In terms of aberrations, the optical system 60 in FIGS. 6 and 7 shows a negative amount of defocus.

When a negative amount of defocus occurs with the natural lens 16, it is known medically as hypermetropia, or farsightedness, and can be remedied by spectacles, a contact lens or a phakic lens that introduces positive optical power into the eye's optical system, thereby decreasing the effective focal length of the system and axially translating the image 64 back toward the retina 22.

For a single focal length IOL, a focal length is typically chosen to correct for relatively distant objects, and close objects appear as blurry without additional spectacles or contact lenses.

In addition to defocus, an intraocular lens can reduce astigmatism in the eye. Astigmatism occurs when the optical power along one axis differs from the optical power along a different axis, leading to a rotationally asymmetric wavefront. For instance, the optical power along a vertical axis may be envisioned by blocking all the light in the pupil of the eye except a thin vertical slice through the center of the lens. Similar situations hold for a horizontal axis, or any other orientation between vertical and horizontal. The astigmatism may be corrected by adding a cylindrical component of power to the IOL along a particular axis, so that the wavefront that strikes the retina is essentially rotationally symmetric. The correction of astigmatism is well-known, and is straightforwardly accomplished in IOLs, as well as spectacles and some contact lenses.

As a further improvement to an intraocular lens in which defocus and astigmatism are reduced, spherical aberration may be reduced. In general, for a lens that has a finite amount of spherical aberration, the optical power at the edge of the lens is different from the optical power at the center of the lens. A bundle of rays originating from a single point on the object, after passing through a lens with spherical aberration, does not converge to a single point on the image, but blurs by an amount in proportion to the amount of spherical aberration. FIG. 8 shows an optical system 80 with positive spherical aberration. For a lens 81 with positive spherical aberration, the edge of the lens has more optical power than the center of the lens. A bundle of rays 84 originating at the base of the object 83 passes through the aberrated lens 81, and does not come to a sharp focus at the retina 82. Rather, the rays passing through the edge of the lens 81 converge more quickly than the rays passing through the center of the lens 81, leading to a blur at the retina 82. Similarly, FIG. 9 shows an optical system 90 with negative spherical aberration, in which the lens 91 has less optical power at its edge than at its center. For a bundle of rays 94 originating from the base of the object 93 and passing through the aberrated lens 91, rays passing through the edge of the lens 91 converge less quickly than rays passing through the center of the lens 91, leading to a blur at the retina 92. In general, spherical aberration is rotationally symmetric about the optical axis. Spherical aberration is also independent of field height or field angle, so that a bundle of rays originating from the edge of the object would exhibit the same amount of spherical aberration as a bundle originating from the base.

There are known ways to reduce spherical aberration in IOLs. For instance, U.S. Pat. No. 6,609,793, incorporated by reference in its entirety herein, discloses a method of designing an ophthalmic lens. First, at least one of the surfaces of the cornea is characterized as a mathematical model. Then, the model is used to calculate the aberrations of the surface or surfaces. Finally, the lens is modeled to reduce the aberrations for at least one of the foci, for an optical system that includes the lens and at least one of the surfaces of the cornea. In particular, the publication discloses reducing to essentially zero the eleventh Zernike coefficient, which corresponds to third-order spherical aberration. Additional correction is disclosed in U.S. patent application Ser. No. 10/724,852, and U.S. Pat. No. 6,705,729, which are each herein incorporated by reference in their entirety.

In addition to spherical aberration, another wavefront aberration that degrades the image at the retina is coma. The general characteristics of coma are rotationally asymmetric, and are therefore difficult to draw in simple figures in the manner of exemplary FIGS. 2-9. Instead, a picture of an exemplary wavefront aberrated by coma is shown in FIG. 10. An observer located at the retina, looking at the lens, sees an aberrated wavefront 104 propagating toward him. For comparison, an unaberrated wavefront 103 is shown, superimposed on the aberrated wavefront 104. Along an axis 102, denoted by "x", the two wavefronts 103 and 104 coincide. Along an axis 101, denoted by "y" and perpendicular to axis 102, the aberrated wavefront 104 shows an odd-order departure from the unaberrated wavefront 103. Third-order coma shows a cubic dependence in the wavefront departure along axis 101, fifth-order coma shows a fifth-order dependence, and so forth for higher odd-orders of coma. Although "x" and "y" are drawn as horizontal and vertical in FIG. 10, in reality the coma axes may have any orientation.

For a bundle of off-axis rays originating at a single point on the object, the rays converge to a cone-shaped blur at the image. Rays passing through the center of the aberrated lens arrive at the point of the cone, with the remainder of the bundle of rays filling out the characteristic cone shape. The orientation of the cone is radial with respect to the optical axis, and the size of the cone increases with distance away from the optical axis.

For a human eye 10 with good vision, the total amount of coma is generally fairly small. However, the cornea 13 and natural lens 16 may individually have substantial amounts of coma of opposite sign, which offset each other when light passes through both elements sequentially. When the natural lens 16 is removed and replaced with an IOL, the coma of the cornea 13 may become significant, so that if the cornea's coma is not corrected by the IOL, it may degrade the vision of the eye.

Accordingly, there exists a need for an intraocular lens that corrects for the coma of the cornea. When implanted, such an IOL reduces the amount of coma in the optical system of the eye (cornea and IOL together), and improves the vision of the eye.

BRIEF SUMMARY OF THE INVENTION

An embodiment is a method of specifying the anterior surface and the posterior surface of a lens for implantation in an eye having a cornea, comprising: performing at least one measurement on the eye; determining an optical power from the at least one measurement; and determining an anterior radius and a posterior radius from the optical power, wherein the anterior radius and the posterior radius minimize the coma of the eye; and determining at least one aspheric term for at least one of the anterior surface and the posterior surface; whereby the coma of the lens offsets the coma of the cornea; and whereby the anterior surface and the posterior surface are specified by the anterior radius, the posterior radius and the at least one aspheric term.

A further embodiment is a method of specifying the anterior surface and the posterior surface of a lens for implantation in the eye of a patient, comprising: performing a measurement capable of determining an optical power, P, of the lens; determining a shape factor, X, from the optical power; determining an anterior radius, Ra, and a posterior radius, Rp, from the shape factor and the optical power; and determining at least one aspheric term for at least one of: the anterior surface and the posterior surface; whereby the anterior surface and the posterior surface are specified by the anterior radius, the posterior radius and the at least one aspheric term.

A further embodiment is a lens having an optical power for implantation in an eye having a cornea, comprising: an anterior surface having an anterior radius; and a posterior surface having a posterior radius; wherein the anterior radius and the posterior radius determine the optical power; and wherein the anterior radius and the posterior radius are selected to minimize coma of the eye for the value of optical power; whereby the coma of the lens offsets the coma of the cornea. Optionally, existing ocular coma, originating in the cornea and the natural lens, may be corrected with a phakic lens.

A further embodiment is a lens having an optical power and a shape factor for implantation in an eye having a cornea, comprising: an anterior surface having an anterior radius, Ra; and a posterior surface having a posterior radius, Rp; wherein the anterior radius and the posterior radius determine the optical power, P, and the shape factor, X; and wherein the shape factor minimizes the coma of the eye for the value of optical power; whereby the coma of the lens offsets the coma of the cornea.

A further embodiment is an intraocular lens having an optical power, comprising: an anterior surface having an anterior radius; and a posterior surface having a posterior radius; wherein the anterior radius and the posterior radius determine the optical power; and wherein the anterior surface is concave; and wherein the posterior surface is convex.

A further embodiment is an intraocular lens having an optical power and a shape factor, comprising: an anterior surface having an anterior radius; and a posterior surface having a posterior radius; wherein the anterior radius and the posterior radius determine the optical power and the shape factor; and wherein the shape factor is less than −1.

BRIEF DESCRIPTION OF THE SEVERAL VIEWS OF THE DRAWINGS

FIG. 14 is an exemplary spreadsheet that performs a paraxial ray trace on the system of FIG. 13.

DETAILED DESCRIPTION OF THE INVENTION

Figure 1:
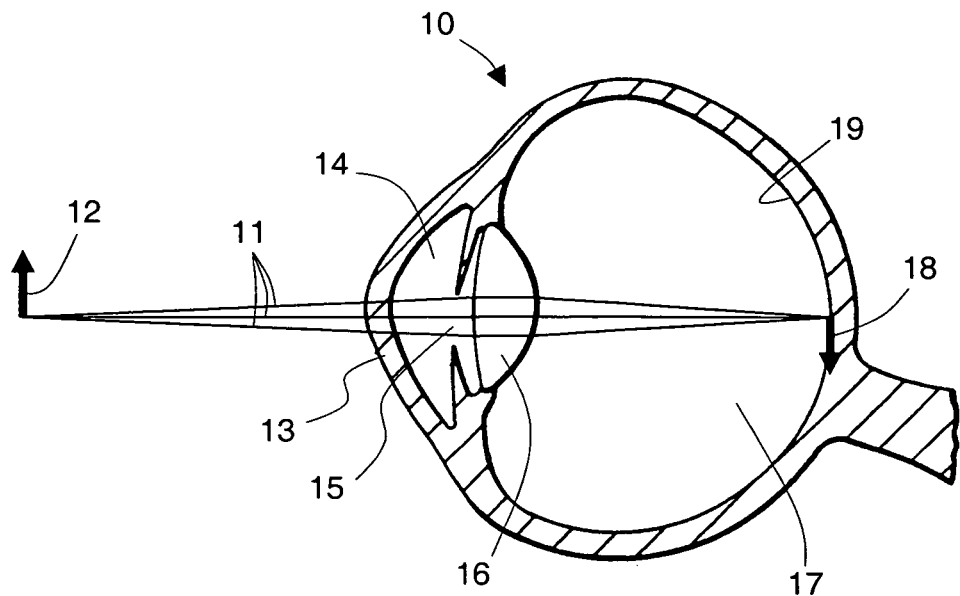
FIG. 1 is a cross-section of a human eye.
Figure 2:
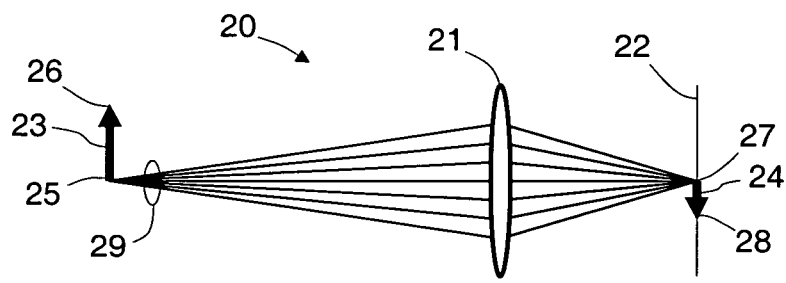
FIG. 2 is a schematic drawing of an aberration-free optical system, with an on-axis bundle of rays.
Figure 3:
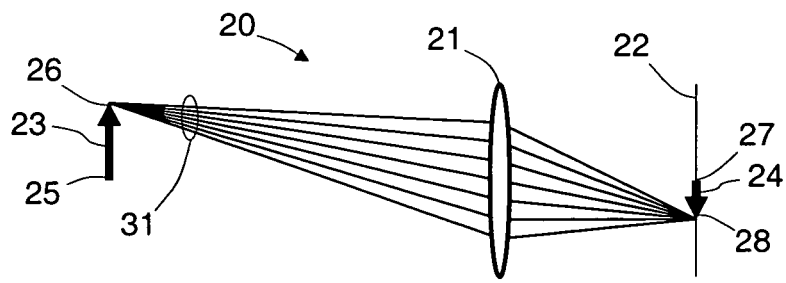
FIG. 3 is a schematic drawing of the optical system of FIG. 2, with an off-axis bundle of rays.
Figure 4:
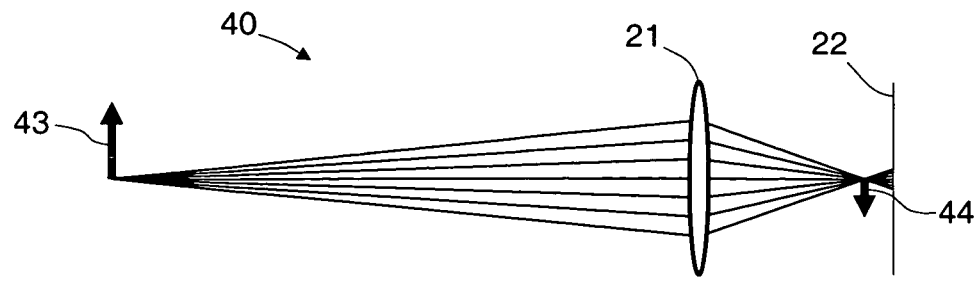
FIG. 4 is a schematic drawing of an optical system with positive defocus, with an on-axis bundle of rays.
Figure 5:
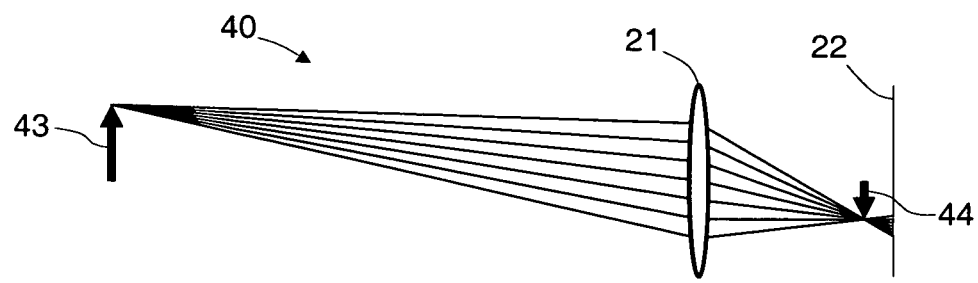
FIG. 5 is a schematic drawing of the optical system of FIG. 4, with an off-axis bundle of rays.
Figure 6:
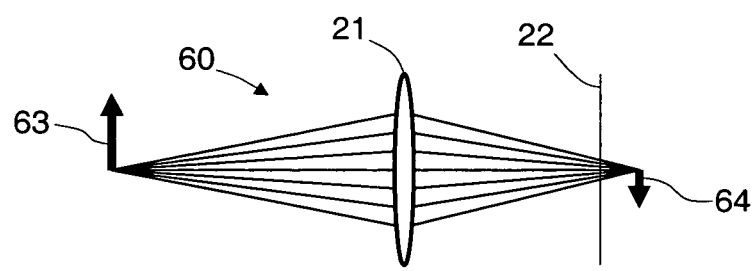
FIG. 6 is a schematic drawing of an optical system with negative defocus, with an on-axis bundle of rays.
Figure 7:
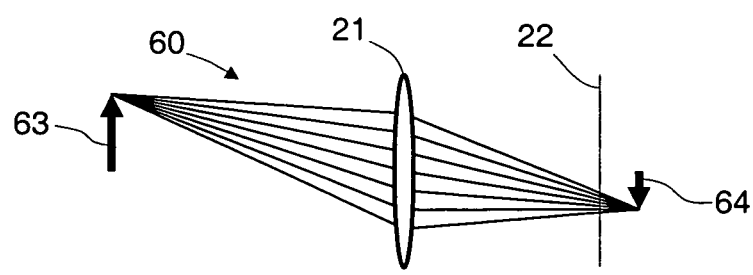
FIG. 7 is a schematic drawing of the optical system of FIG. 6, with an off-axis bundle of rays.
Figure 8:
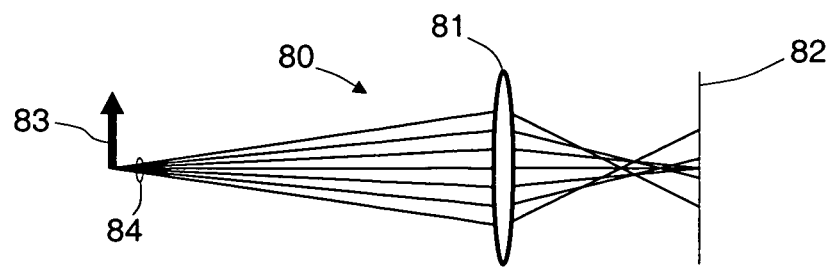
FIG. 8 is a schematic drawing of an optical system with positive spherical aberration.
Figure 9:
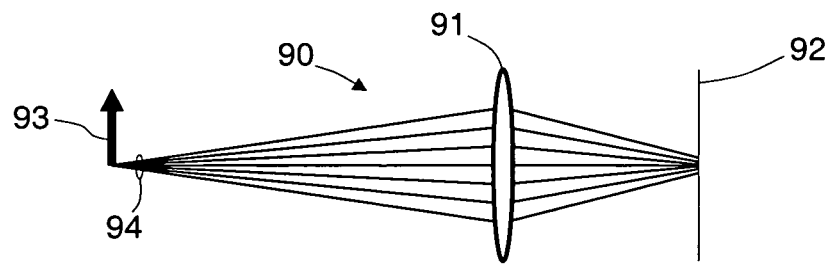
FIG. 9 is a schematic drawing of an optical system with negative spherical aberration.
Figure 10:
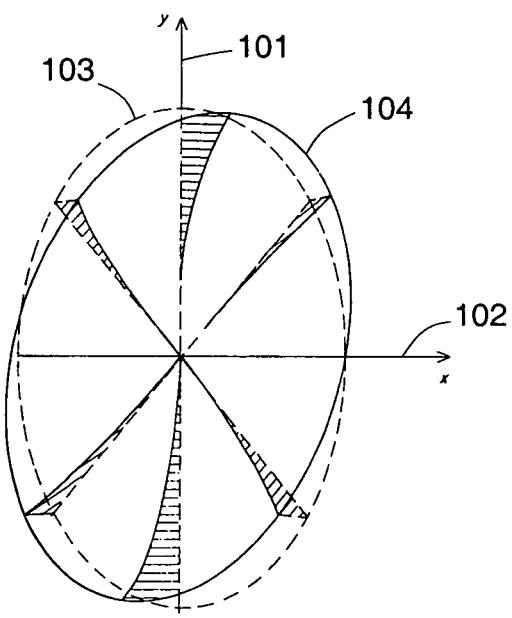
FIG. 10 is a schematic drawing of an aberrated wavefront exhibiting coma.

A process is detailed below for designing an intraocular lens that reduces the coma of the eye's optical system, which gives better off-axis performance of the lens, as well as relaxed manufacturing and alignment tolerances. The process is broken into several general steps, some of which are given their own sections below. The steps may be performed in any order.

First, a series of measurements are performed on the patient. Typically, the spherical radius of curvature of the anterior cornea is measured, or optionally the anterior and posterior corneal surfaces, as well as the axial length (i.e., the distance between the cornea and the retina). Optionally, more measurements may be taken, or various other properties may be measured, such as a wavefront mapping of the cornea, axial length and anterior chamber depth. One goal of these patient measurements is to predict the required optical power of the intraocular lens.

Second, the patient measurements are used to predict the required power of the IOL. In the section below titled, "CALCULATION OF REQUIRED INTRAOCULAR LENS POWER", as an example, a thin-lens formalism is described that converts the measured values of axial length and corneal radius into a required optical power.

Third, once a particular required optical power is established, a preferred shape factor X is determined that minimizes the coma of the total eye system. The shape factor X describes the base spherical radii of the lens surfaces independent of the power of the lens. The shape factor X attains its preferred value when the third-order coma of the lens best offsets the third-order coma of the cornea, and reduces the third-order coma of the total optical system of the eye. The formalism for determining the preferred shape factor X uses a paraxial model and/or a real raytracing model, and is described in detail in the section titled, "RAYTRACING MODEL". Once the model is established, the values of the preferred shape factor X are given in the section titled, "OPTIMAL LENS SHAPE FOR A GIVEN POWER".

Fourth, optionally, once a power is selected and a preferred shape factor X is determined, one or more aspheric and/or conic terms are added to one or both of the lens surfaces, so that spherical aberration is reduced and on-axis performance is improved. The adding of aspheres is detailed in the section titled, "OPTIMIZING AN INTRAOCULAR LENS DESIGN". Designs for several values of power are carried to completion and are presented in the section titled, "SAMPLE DESIGNS".

Calculation of Required Intraocular Lens Power

This section describes an example of a known method (one of many known methods) of calculating the required power (or, equivalently, focal length) of an intraocular lens (IOL); based on a geometrical optics-based formula and several measured input values.

The calculations are performed using a paraxial raytrace, with four surfaces: (1) spectacles, (2) the cornea, (3) the intraocular lens, and (4) the retina. For the purposes of this calculation, each of these four surfaces is assumed to be an infinitely thin surface or thin lens having a particular power. The numerical values used in the calculations may vary depending on the preference of the practitioner, but the thin lens methodology remains essentially unchanged. Each of these surfaces is described in more detail below.

Given the power $\phi$ of each surface, the refractive index n between the surfaces, and thickness t between the surfaces, one may use the well-known paraxial refraction and transfer equations to trace a ray through the optical system of the eye.

The paraxial refraction equation predicts the exiting ray angle (relative to the optical axis) u', after refraction at a surface with power $\phi$:

$$n'u'=nu-y\phi,$$

where u is the incident ray angle, y is the incident and exiting ray height at the surface, and n and n' are the incident and exiting refractive indices, respectively. The refractive indices are dimensionless, the ray angles are in radians, the ray heights are in mm [or, alternately, m], and the surface powers are in $mm^{-1}$ [or, alternately, diopters].

The paraxial transfer equation predicts the ray height y' at a surface, after propagation by a distance t between a previous surface and the current surface:

$$y'=y+tu,$$

where y is the ray height at the previous surface and u is the ray angle (relative to the optical axis) between the previous surface and the current surface. The ray angle is in radians and the ray heights and distances are both in mm [or, alternately, both in m].

Figure 11:
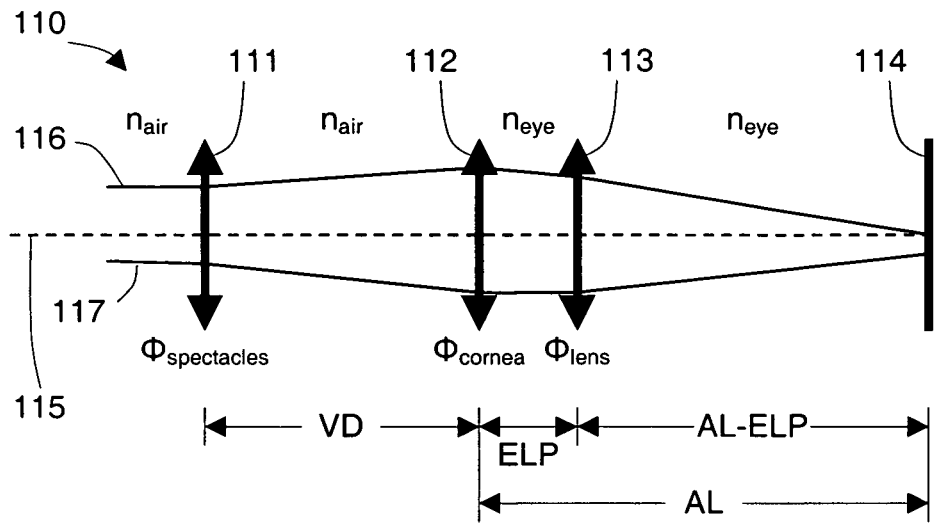
FIG. 11 is a schematic drawing of a thin lens system used to calculate the required optical power of an intraocular lens.

The above paraxial refraction and transfer equations are alternately used to trace rays through a multi-surface optical system. FIG. 11 shows a schematic drawing of the thin lens system 110 used for predicting the required power of an intraocular lens. Rays originate at a distant object (not shown), pass through the spectacles 111, the cornea 112, the intraocular lens 113, and strike the retina 114. Here, optical elements 111-113 are assumed to be rotationally symmetric about the optical axis 115. For the purpose of predicting a required intraocular lens power, the equations should be used to trace a marginal ray 116 through the system, as follows. An object is assumed to be at infinity, so a marginal ray 116 originating at the base of the object arrives at the spectacles 111 with a ray angle u of 0 and a non-zero ray height y (with a value typically proportional to the pupil diameter, but unimportant for predicting the required intraocular lens power).

This marginal ray 116 is then traced from the object at infinity in refractive index $n_{air}$, through the spectacles 111 with power $\phi_{spectacles}$, along a distance VD ("vertex distance") in refractive index $n_{air}$ to the cornea 112, through the cornea 112 with power $\phi_{cornea}$, along a distance ELP ("effective lens position") in refractive index $n_{eye}$ to the intraocular lens 113, through the intraocular lens 113 with power $\phi_{lens}$, and finally along a distance AL-ELP ("axial length" minus "effective lens position") in refractive index $n_{eye}$ to the retina 114. The marginal ray 116 is forced to have a ray height of zero at the retina 114, ensuring that the infinitely-distant object forms an in-focus image at the retina 114. Note that the refraction and transfer equations may also be used to trace any ray 117 through the system 110, and may be used to predict first-order performance of the optical system in the presence of deviations from the nominal layout shown in FIG. 11.

The trace of the marginal ray may be performed analytically, yielding the following value for the required power of the intraocular lens $\phi_L$:

$$\phi_{lens} = \frac{n_{eye}}{AL - ELP} - \frac{n_{eye}}{\frac{n_{eye}}{\frac{n_{air}}{\frac{n_{air}}{\phi_{spectacles}} - VD} + \phi_{cornea}} - ELP}$$

In practice, the value of axial length is measured for each patient, along with the radius of curvature of the cornea and, optionally, the corneal thickness. Details of these measurements and numerical examples follow.

The vision of the patient is typically corrected so that once the intraocular lens is implanted, the patient will have a small amount of residual defocus, which is well-corrected by spectacles with −0.5 diopters of power. Because an eye with an intraocular lens can no longer accommodate, it can no longer bring objects at various distances into focus on the retina. Instead, objects only at a particular distance from the eye are in sharp focus, while objects at increasing distances away from that distance become increasingly out of focus. Typically, the most desirable scenario for the patient is analogous to nearsightedness, in which the patient wears a pair of weak, negative-power spectacles. The spectacles form virtual images of distant objects, where the images are much closer to the eye than the objects themselves, and are closer to the particular distance at which the eye is nominally focused. The power of the spectacles is typically chosen to be −0.5 diopters, which is a relatively weak prescription; patients requiring such a prescription may have measured vision of 20/25 or 20/30 without the spectacles. This value of −0.5 diopters may sometimes be referred to as the "desired refraction" or "desired power" of the eye once the intraocular lens has been implanted. Note that this target value may vary from surgeon to surgeon, and that many surgeons also aim for emmetropia for distant objects. Other powers may be used, including a value of zero diopters.

For the purposes of the IOL power calculation, the spectacles are assumed to be a thin lens in air with a power of −0.5 diopters (or, equivalently, a power of −0.0005 mm$^{-1}$, with an effective focal length in air of −2000 mm). The on-axis distance between the spectacles and the cornea, often referred to as the "vertex distance", is commonly chosen to be 14 mm, although values between about 12 mm and about 14 mm are typical. The refractive index before and after the spectacles is that of air, and is taken to be 1.

An actual cornea has two curved surfaces—an anterior surface facing air, and a posterior surface facing the retina—in addition to a characteristic refractive index of about 1.3771 between the two curved surfaces. However, for the purpose of the thin lens model used to predict the required power of the intraocular lens, the cornea is taken to be a single curved surface, with a incident refractive index $n_{air}$ of 1, an exiting refractive index $n_{cornea}$ of about 1.3375, and a radius of curvature that is measured for each patient. The radius of curvature of the cornea is measured by any one of a known number of methods, including but not limited to, manual or automated keratometry, corneal topography, the trial hard contact lens method, and the calculated method. The result of each of these measurement methods is typically a single value of radius of curvature, $R_{cornea}$, which is inserted into a formula that predicts the required intraocular lens power. Optionally, the practitioner may measure the radius of curvature along different directions, in order to predict, and subsequently correct for, astigmatism. In addition, the practitioner may measure the anterior radius of the cornea and the corneal thickness, and may use these values to predict a value of required power.

For the model, the cornea is then assumed to be a single, infinitely-thin surface, with an optical power of $(n_{cornea} - n_{air})/R_{cornea}$. A typical measured value for the radius of curvature of the cornea is about 7.704 mm, which yields a typical power of $(1.3375-1)/(7.704 \text{ mm}) = 0.0438 \text{ mm}^{-1}$, or 43.8 diopters.

For the model, the incident medium for the cornea is air, with a refractive index of 1. The exiting medium of the cornea is typically chosen to be the refractive index of the eye $n_{eye}$, with a value of roughly 1.336. Note that the value of $n_{cornea}$ is used only to calculate the power of the cornea, and is not used at its exiting medium. In tracing rays between the cornea and the lens, the refractive index is taken to be $n_{eye}$, or about 1.336.

The iris of the eye is located adjacent to the cornea, with a separation referred to as the "anterior chamber depth", typically about 3.74 mm. However, for the purposes of the intraocular lens power calculation, the iris is neglected and is not included in the model.

After the cornea, the refractive index $n_{eye}$ is about 1.336. The intraocular lens itself is assumed to be a thin lens, separated from the cornea by a distance referred to as the "effective lens position". The effective lens position is set during the implantation surgery, and is typically as close to 5.25 mm as possible. Although small errors in the effective lens position are inevitable, the ever-evolving surgical methods and skill of the practitioner ensure that these errors are minimized. Any residual errors that do arise in the effective lens position may be subsequently corrected by changing the prescription of the spectacles worn by the patient. Note that the actual structure of the lens, including its curvatures and refractive index, are not determined by this power-selection process, which yields only the power of the lens when used in a refractive index $n_{eye}$ of about 1.336. In practice, the intraocular lenses may be available only in discrete values of power, and the practitioner may choose to vary the effective lens position during the implantation surgery, so that an off-the-shelf value of lens power may be used. Common, off-the-shelf, intraocular lenses are available from powers of 5 diopters to 30 diopters, in increments of 0.5 diopters. Some manufacturers may even provide increments as small as 0.25 diopters, or smaller.

The retina is effectively the image plane in this thin lens model, so its specific properties are relatively unimportant. The separation between the cornea and the retina, commonly called the "axial length", is measured for each patient by a known method, such as biometry. The measured axial length commonly falls in a range of 21 mm to 26 mm, although it may fall outside this range. The thin lens model requires a value for the separation between the intraocular lens and the retina, which is the axial length minus the effective lens position. For typical values of axial length and effective lens position, 23.45 mm and 5.25 mm, respectively, a typical separation between the intraocular lens and the retina is about 18.2 mm. The incident refractive index on the retina is $n_{eye}$, or about 1.336.

As a numerical example, consider the following typical values: $n_{air}=1$, $n_{cornea}=1.3375$, $n_{eye}=1.336$, $R_{cornea}=7.704$ mm, $\phi_{cornea}=0.0438$ mm$^{-1}$ (or 43.8 D), $\phi_{spectacles}=-0.0005$ mm$^{-1}$ (or −0.5 D), VD=14 mm, ELP=5.25 mm, and AL=23.45 mm. Inserting these numerical values into the equation for the required power $\phi_{lens}$ of the intraocular lens gives a typical value of 0.0212 mm$^{-1}$ (or 21.2 D).

Figure 12:
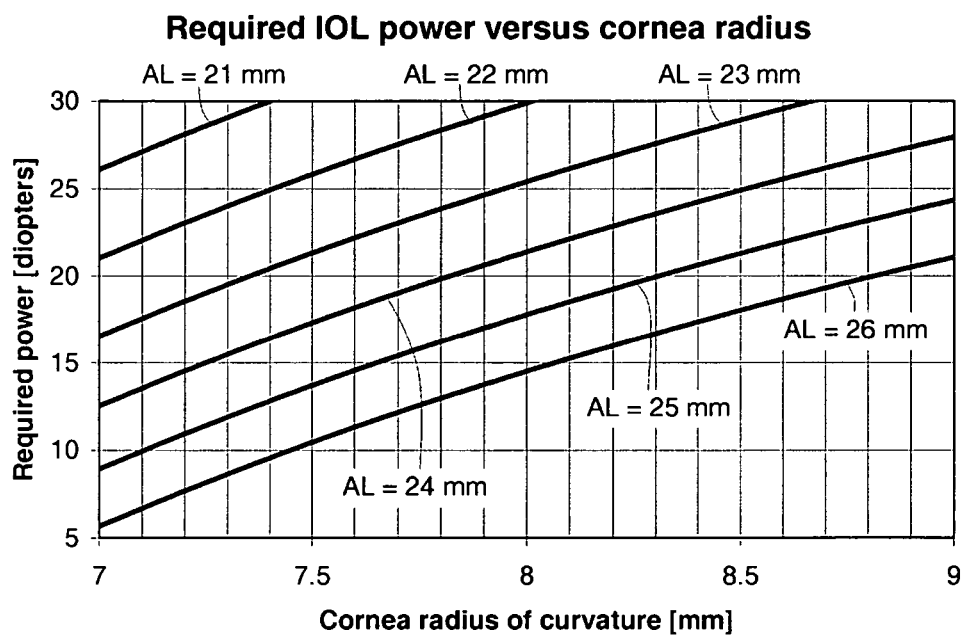
FIG. 12 is a plot of the required optical power of an intraocular lens, as a function of axial length and corneal radius.

As a further example, FIG. 12 shows a plot of the required intraocular lens power, as a function of measured cornea radius. A series of six curves are shown, which correspond to axial lengths in the typical range of 21 mm to 26 mm. The curves are generated using the equation above, and using the nominal values from the previous paragraph.

Over the years, there have been some subtle improvements to some of the non-measured values used in the above equation to predict IOL power. For instance, the axial length may be lengthened to account for the thickness of the retina. Or, the effective lens position may be adjusted to account for the real separation between the front and rear principal planes of the cornea. Or, the refractive index of the cornea may be set to 4/3, 1.33, or any other suitable value. Each of these improvements uses essentially the same thin lens formalism used to derive the above formula, and typically shifts the calculated required IOL power by less than 0.5 D. As a result, these improvements, while important to the field of study, are not discussed further here.

It should be noted that each eye of the patient may be treated individually, with its own measurements of cornea radius and axial length, its own intraocular lens, and its own spectacle prescription. Each lens in a pair of spectacles corresponds to its own eye.

Note that the value of power (or, equivalently, focal length) is a first-order property. Other appropriate first-order properties, such as defocus or image translation caused by decentration, may be calculated by using the paraxial raytracing formalism described above. Third-order properties, such as spherical aberration, coma, astigmatism, field curvature and distortion, may also be treated in a limited manner by the paraxial raytracing formalism. Specifically, the coma of the intraocular lens may be varied without changing the power (or, equivalently, the focal length) of the lens by simultaneously adjusting the radii of curvature of both lens surfaces in a prescribed manner. Because the coma of the intraocular lens is adjustable, it may be used to offset, reduce or cancel the coma of the cornea. As a result, the image at the retina may have improved quality by having a reduced amount of coma.

The following section describes a more powerful paraxial model than the analytical formula presented above, and uses it to show the dependence of coma on the shape factor, X, of the intraocular lens.

Raytracing Model

The analytical formula presented previously to predict the required power for an intraocular lens is convenient and easy to use, but is not powerful enough to make predictions about coma or the shape factor, X, of the lens. For this task, a more generalized raytrace is performed. The system under consideration is shown in FIG. 13.

The calculations may be performed by a commercially-available raytracing program, such as Oslo, ZEMAX, Code V, and others. Indeed, many of the plots that follow are generated using Oslo, which can easily perform a ray trace of the system, including aspheric or conic terms, and can output third-order coma coefficients.

In addition to the exact ray trace performed by Oslo, a spreadsheet is shown in FIG. 14 that performs a paraxial raytrace of the system. A paraxial raytrace is mathematically simpler to perform than a real raytrace, and yields very similar results for the optical system of the eye. Both the schematic system of FIG. 13 and the mathematics used in the ray trace spreadsheet of FIG. 14 are described in detail below.

Figure 13:
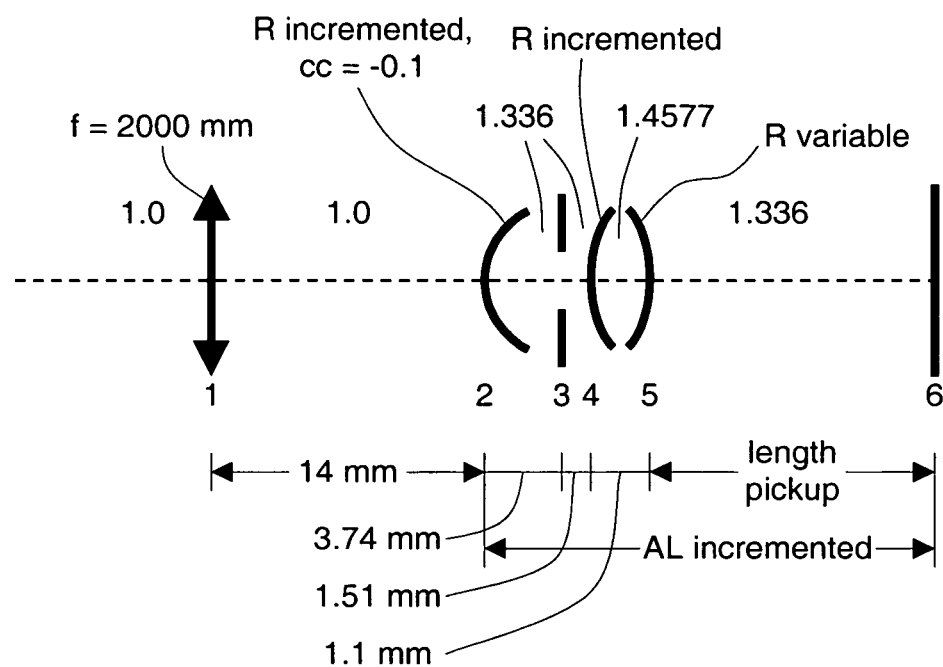
FIG. 13 is a schematic drawing of an optical system that simulates use of an intraocular lens.
Figure 15:
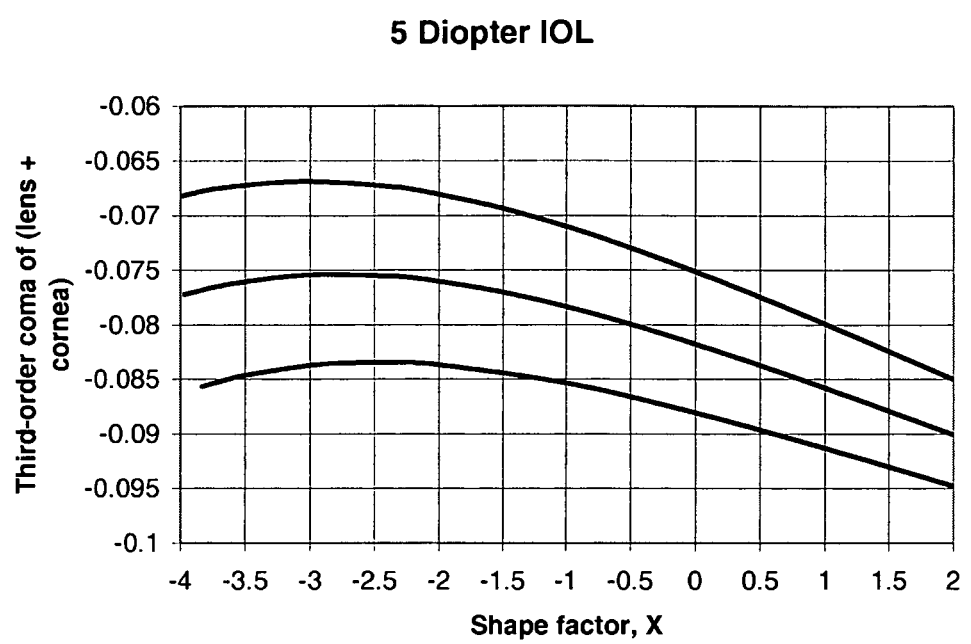
FIG. 15 is a graph of the third-order coma versus shape factor X for a 5 D intraocular lens.
Figure 16:
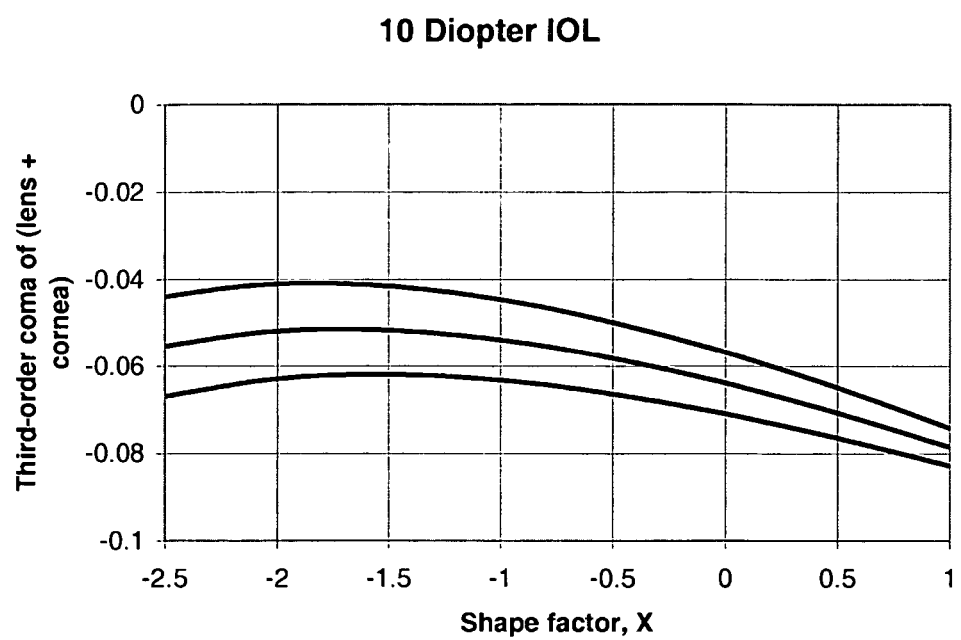
FIG. 16 is a graph of the third-order coma versus shape factor X for a 10 D intraocular lens.
Figure 17:
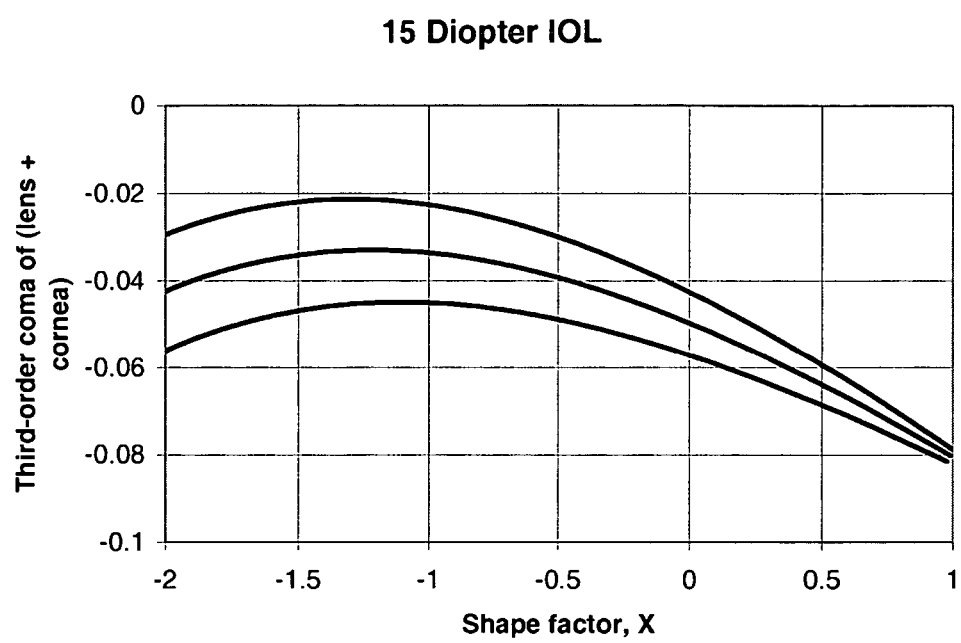
FIG. 17 is a graph of the third-order coma versus shape factor X for a 15 D intraocular lens.
Figure 18:
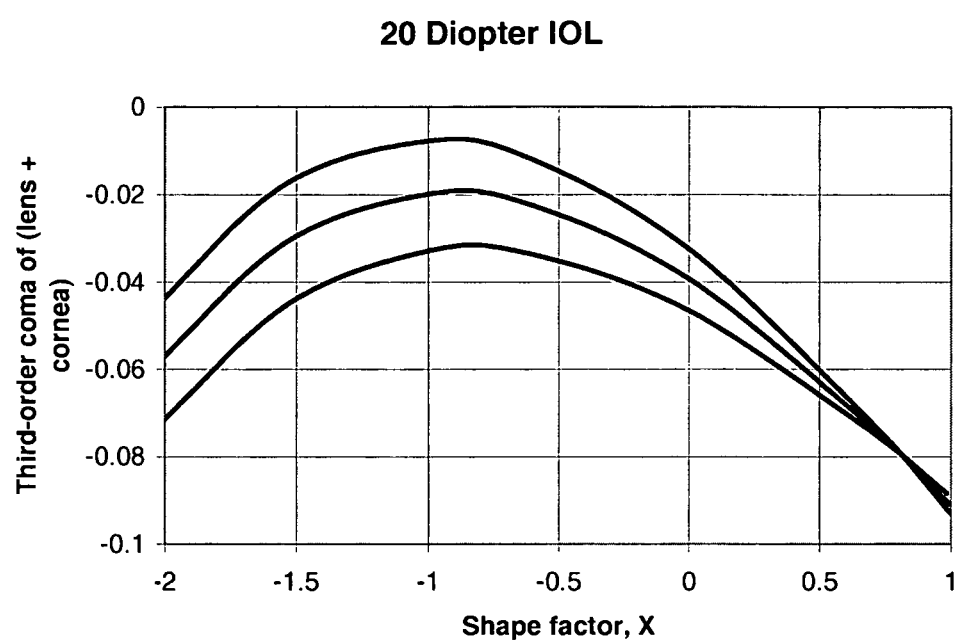
FIG. 18 is a graph of the third-order coma versus shape factor X for a 20 D intraocular lens.
Figure 19:
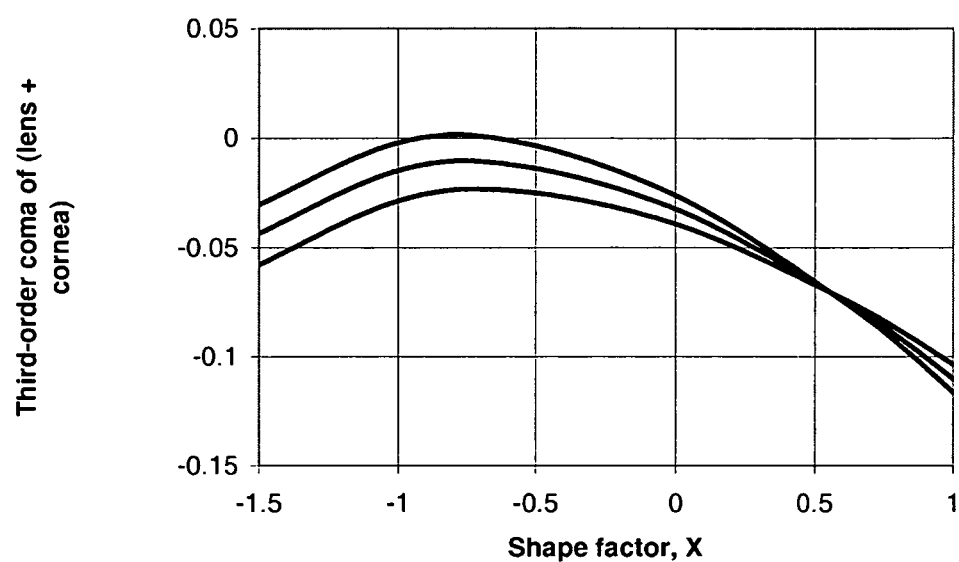
FIG. 19 is a graph of the third-order coma versus shape factor X for a 25 D intraocular lens.
Figure 20:
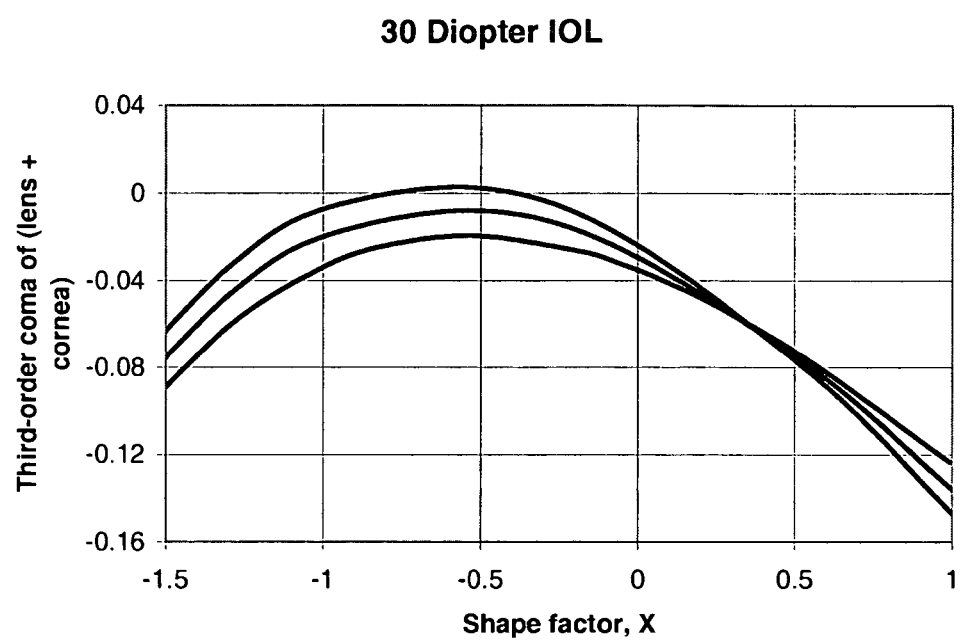
FIG. 20 is a graph of the third-order coma versus shape factor X for a 30 D intraocular lens.

The layout of the spreadsheet is the same as the system shown in FIG. 13, in which light propagates from a distant object, through the spectacles at the leftmost part of the optical system, from left-to-right, until it is collected at the retina at the rightmost part of the optical system. The spectacles are optional in this example. Each surface in the optical system is explicitly treated in the spreadsheet. Input values in the spreadsheet are entered in the thick-boxed cells. All other cells are calculated.

The optical system is entered as a series of surfaces. Each surface is described by a radius, R, a curvature, c=1/R, or in the case of the spectacles, a power, $\phi$ (phi). Each surface has an incident and an exiting refractive index, n and n', respectively, so that the power $\phi$ of each surface is numerically equal to (n'−n)/R. Note that for a flat (i.e. plano or planar) surface, the power and curvature both equal zero, and the radius is infinite. For the purposes of this document, an equation or calculation step that yields an infinite value for a radius of a surface implies that the surface is flat, and that the surface may have additional optional aspheric terms even though its radius is infinite. Each surface is separated by a thickness, t.

Two rays are traced through the system, each with its own height y at each surface, and propagation angle u between surfaces. The specific rays in FIG. 13 are in accordance with standard geometrical optical conventions, and are designated as a marginal ray and a chief ray. The paraxial refraction equation predicts the exiting ray angle (relative to the optical axis) u', after refraction at a surface with power $\phi$:

$$n'u'=nu-y\phi,$$

where u is the incident ray angle, y is the incident and exiting ray height at the surface, and n and n' are the incident and exiting refractive indices, respectively. The refractive indices are dimensionless, the ray angles are in radians, the ray heights are in mm [or, alternately, m], and the surface powers are in mm$^{-1}$ [or, alternately, diopters].

The paraxial transfer equation predicts the ray height y' at a surface, after propagation by a distance t between a previous surface and the current surface:

$$y'=y+tu,$$

In this manner, a ray is given a set of initial conditions at a surface, and is then propagated throughout the optical system.

A marginal ray originates from the base of the object and passes through the edge of the entrance pupil. Because the object is infinitely far away, the marginal ray enters the optical system with a ray angle of 0, and a height of 3 mm, equal to the half the entrance pupil diameter. Any suitable entrance pupil diameter may be used.

A chief ray passes through the center of the aperture stop, with an angle at the stop chosen so that the chief ray angle in object space equals the field of view in object space. The true chief ray angle in object space is the tangent of the ray angle, ubar. Note that the chief ray is set at the aperture stop, then propagated in both directions away from the aperture stop. The paraxial refraction and transfer equations above are easily inverted to trace rays backwards through the system.

Aberrations in the system arise from three distinct surfaces: the cornea, and both the anterior and posterior surfaces of the intraocular lens. The spreadsheet shows the third-order coma contribution for each surface, as well as two intermediate quantities that are used to calculate the coma contributions. A quantity, "A", is defined as ni, the product of the refractive index n before a surface, and the incident angle i of the marginal ray at the surface. Mathematically, "A" is calculated at each surface by the formula $$A = nu + nyc,$$

where n is the refractive index before the surface, u is the propagation angle of the marginal ray before the surface, y is the marginal ray height at the surface, and c is the curvature of the surface. A is dimensionless. Note that A may also be calculated using the numerical values of n and u after the surface, rather than before; both ways produce numerically equal results.

Similarly, a quantity "B" is defined as nibar, the product of the refractive index n before a surface, and the incident angle ibar of the chief ray at the surface. Mathematically, "B" is calculated at each surface by the formula $$B = nu\text{bar} + ny\text{bar}c,$$

where n is the refractive index before the surface, ubar is the propagation angle of the chief ray before the surface, ybar is the chief ray at the surface, and c is the curvature of the surface. B is also dimensionless, and may also be calculated using the numerical values of n and ubar after the surface, rather than before.

The third-order coma contribution $W_{131}$ for each surface is given by $$W_{131} \text{ contribution} = -\frac{1}{2}(y)(A)(B)(u'/n' - u/n)/\lambda,$$

where y is the marginal ray height at the surface, A and B are defined above for the surface, u is the marginal ray angle before the surface, u' is the marginal ray angle after the surface, n is the refractive index before the surface, n' is the refractive index after the surface, and λ is the wavelength. For all these calculations, a wavelength is chosen of 555 nm, which is the peak of spectral luminous efficacy for photopic vision. Optionally, other wavelengths may be used. The total amount of $W_{131}$ is then the sum of these individual surface contributions. These $W_{131}$ contributions are comparable to those produced by Oslo's "Seidel Wavefront Aberration Coefficients", which are accessible through the "seiwvf" command.

Given the calculation instructions above, it is helpful to now describe the system of FIG. 13 in detail surface by surface.

The incident medium is air, with a refractive index $n_{air}$ chosen to be 1. An object is infinitely far away, so that the marginal ray enters the spectacle with a ray angle of 0 and a height of 3 mm, equal to half the entrance pupil diameter. Alternately, the spectacle may be left out of the calculation and the eye assumed to be emmetropic or targeted at emmetropia.

The spectacle, surface 1, is modeled as an aberration-free thin lens with a power of −0.5 diopters. In Oslo, a "perfect" lens is used. In the spreadsheet, a single surface is used, with a power chosen to be −0.5 diopters.

The beam propagates in air (n=1) from the spectacle to the cornea, a distance equal to the vertex distance, in this case assumed to be 14 mm.

The cornea, surface 2, is modeled as a single, curved surface. The radius is used as an input in the spreadsheet, and typical values between 7 mm and 9 mm adequately cover the range of real cornea radii. Unlike the analytical formula, in which the cornea is given its own designated refractive index, the refractive index after the cornea surface in this raytracing model is the refractive index of the eye, $n_{eye}$, chosen to be 1.336. Alternatively, the refractive after the cornea may be given a value different from $n_{eye}$, such as 1.3375, although this change would produce only slight changes in the design presented below.

The conic constant of the cornea varies significantly. For modeling purposes a conic constant between −0.2 and 0.0 is used. This conic constant is used as an input in Oslo in addition to the radius, but the spreadsheet cannot accommodate the conic constant. It is found that a non-zero conic constant merely increases the absolute value of the third-order coma produced by the cornea. In many cases, the intraocular lens cannot generate enough coma to completely offset that of the cornea, so that the optimal shape of the intraocular lens is the shape at which the third-order coma is brought closest to zero. For these cases, the optimal lens shape is independent of the conic constant value, since the coma produced by the cornea is independent of the lens shape. This is discussed in more detail below; for now, it is sufficient to note that the paraxial spreadsheet and the real raytrace in Oslo give excellent agreement for preferred lens shape.

The beam propagates from the cornea to the iris, denoted optically as the aperture stop, surface 3. The distance between them is often referred to as the anterior chamber depth, and is chosen to be 3.74 mm. The refractive index between the cornea and the aperture stop is $n_{eye}$, which is chosen to be 1.336. Other refractive indices and anterior chamber depths may be used here if found to be more suitable. For example, if a two-surface corneal model were used, a refractive index value of 1.3375 would be appropriate.

The aperture stop itself has no optical power, and the refractive index after the stop is the same as before the stop, $n_{eye}$. In Oslo, the user explicitly sets surface 3 to be the aperture stop, with a diameter that floats to accommodate the incident beam size. In the spreadsheet, the aperture stop explicitly starts the raytrace of the chief ray. The chief ray angle through the aperture stop is chosen so that the chief ray angle in object space equals the field of view, or 5 degrees. Alternatively, the field of view may be any other suitable value, such as 10 or 15 degrees.

The beam propagates from the aperture stop, surface 3, to the anterior surface of the intraocular lens, surface 4. The propagation distance is numerically equal to the effective lens position, chosen to be 5.25 mm, minus the anterior chamber depth, chosen to be 3.74 mm, or 1.51 mm. In Oslo, this value is denoted as a "pickup". The refractive index between surface 3 and surface 4 is also $n_{eye}$. Note that the distances and refractive indices chosen are all merely exemplary, and are not restrictive in any way.

The anterior surface of the intraocular lens is spherical, for the purposes of this raytracing model. For a completed IOL design, either or both of the lens surfaces may have one or more aspheric components and/or a conic constant. However, at this stage of the design process, in which the lens performance is characterized by its base radii of curvature, the aspherics and conics are omitted. The numerical value of the radius that is used in the exemplary spreadsheet of FIG. 14 is about 110 mm, which is a relatively large, positive radius. This gives a very shallow, convex curvature to the anterior surface. In the spreadsheet, the value of curvature may be varied by the spreadsheet solver to change the value of a particular cell in the spreadsheet. In our case, we wish to set the value of total third-order coma, $W_{131}$, equal to zero by changing the anterior surface curvature. In Oslo, this value may be either used as a variable, or may be incremented manually (as is done to produce some of the plots that follow).

The distance between the anterior and posterior surfaces of the lens is equal to the lens thickness, nominally about 1.1 mm, for example. This value may vary according to manufacturing techniques and preferences, and is varied manually in several of the plots that follow over the range of 1.0 mm to 1.2 mm. For comparison with the analytical formula presented in the previous section, the thickness may be set to 0. The refractive index of the intraocular lens is chosen to be 1.4577.

The posterior surface of the lens, surface 5, is also spherical in this model. Like the anterior surface, it may have optional aspheric and/or conic components in the final design. In Oslo, the radius is chosen to be a variable, so that during optimization, it is varied to minimize the merit function. In the spreadsheet, the power of the surface is chosen to be a "solve" so that its value automatically sets the marginal ray height to zero at the retina. The required power $\phi$ of the anterior surface is easily calculated from the paraxial transfer and raytrace equations, and is found to be $$\phi = nu/y + n't'/t',$$

where n is the refractive index before the anterior surface (1.4577), u is the marginal ray angle before the anterior surface, y is the marginal ray height at the anterior surface, n' is the refractive index after the anterior surface (1.336), and t' is the distance between the anterior surface and the retina. The curvature c is then found by $c=\phi/(n'-n)$, and the radius R is found by $R=1/c$. Alternatively, the anterior surface could be varied, or both the anterior and posterior surfaces could both vary.

The distance between the anterior surface of the lens and the retina is calculated so that the axial length (i.e., the distance between the cornea and the retina) is a chosen value. The range of 21 mm to 26 mm for the axial length accommodates most patients, although values outside of this range may be used in this model. In the spreadsheet, the value of thickness in the cell is easily calculated. In Oslo, this length is most easily specified as a "length pickup". The refractive index between the lens and the retina is $n_{eye}$.

Surface 6 is the retina. The specific properties of the retina are relatively unimportant for this particular model. The important quantity at the retina is its incident refractive index (1.336). It is important to note on the spreadsheet that the marginal ray height at the retina is zero, thereby ensuring that an infinitely distant object forms an image at the retina itself, rather than before or after the retina surface.

From the spreadsheet, several paraxial constants for the complete eye system may be readily calculated. The effective focal length f' in image space is given by $f'=-y/u'$, where y is the incident marginal ray height, and u' is the exiting marginal ray angle. The numerical aperture NA is given by $NA=|n' \sin u'|$, where n' is the exiting refractive index (1.336), and u' is the exiting marginal ray angle. The Lagrange invariant L is calculated by $L=(n)(ubar)(y)-(n)(u)(ybar)$, where n is the refractive index, u is the marginal ray angle, y is the marginal ray height, ubar is the chief ray angle, and y is the chief ray height. The Lagrange invariant may be calculated before or after any surface in the system. All of these quantities are also evaluated in Oslo, with minor differences arising from the fact that Oslo uses a real raytrace while the spreadsheet uses a paraxial raytrace.

There are several properties of an intraocular lens that may be calculated by a thin-lens analysis, assuming a thickness of zero. For instance, the formula for required IOL power presented earlier is calculated in this manner. In addition, a conjugate factor Y, may be calculated. The conjugate factor Y of a thin lens is defined as $Y=(u'+u)/(u'-u)$, where u is the incident marginal ray angle, and u' is the exiting marginal ray angle. For the thin lens shown schematically in FIG. 11, the conjugate factor Y is found to be $$Y = \frac{2 \cdot n_{eye}}{\Phi_{IOL}(AL - ELP)} - 1$$

This value is calculated and displayed numerically in the spreadsheet.

The values of IOL power and conjugate factor are also calculated using the real value of the lens thickness (usually in the range of 1.0 mm to 1.2 mm). The IOL power $\phi$ is given by $$\phi = \phi_{anterior} + \phi_{posterior} - (t_{lens}/n_{lens})(\phi_{anterior})(\phi_{posterior}).$$

The conjugate factor is given by its defining equation above.

The shape factor, X, of the intraocular lens is calculated from the curvatures of the anterior and posterior surfaces, $c_{anterior}$ and $c_{posterior}$, by $$X = (c_{anterior} + c_{posterior})/(c_{anterior} - c_{posterior}).$$

Equivalently, the shape factor, X, may be calculated in terms of the radii of curvature of the anterior and posterior lens surfaces, $R_{anterior}$ and $R_{posterior}$, by $$X = (R_{posterior} + R_{anterior})/(R_{posterior} - R_{anterior}).$$

The model described in this section is then used to calculate the third-order coma of the combination of the cornea and the intraocular lens, and show its behavior as a function of lens shape, X. It is shown below that for each value of lens power, there is a range of preferred shape factor, X, that reduces the absolute value of the total third-order coma in the eye system.

Optimal Lens Shape for a Given Power

For a particular intraocular lens power, there is a range of third-order coma values that can be produced by varying the shape factor, X, of the lens. This section shows the values of coma versus shape factor for intraocular lens powers in the range of 5 diopters to 30 diopters.

These values are calculated in Oslo, although they may also be calculated using the spreadsheet described in the previous section. Oslo was chosen so that the conic constant of the cornea could be set at a non-zero value, specifically −0.1. Note that the paraxial spreadsheet can only accommodate spherical surfaces.

For three values of cornea radius—7 mm, 8 mm and 9 mm—the anterior radius was altered manually to achieve a particular value of X, then the posterior radius was varied during optimization. The only variable was the posterior radius. The only operand in the merit function was "PY", which sets the axial ray height at the retina as close to zero as possible. The values reported and plotted are the Seidel third-order coma coefficients, CMA3. For all plots, the conic constant of the cornea is −0.1 and the thickness of the lens is 1.1 mm. The plots are shown in FIGS. 15-20.

Each of the plots in FIGS. 15-20 shows three curves, where the topmost curve is for $R_{cornea}=9$ mm, the middle curve is for $R_{cornea}=8$ mm, and the bottom curves is for $R_{cornea}=7$ mm. In reality, the actual measured radius of curvature of a patient's cornea is highly likely to fall between 7 mm and 9 mm, so the range subtended by these three curves adequately covers a full range of patients. The embodiments and examples cover a broader range as well. For all the plots, the conic constant of the cornea is −0.1, and the thickness of the lens is 1.1 mm, as an example.

The curves plot the reported value of third-order coma of the whole optical system of the eye versus the shape factor of the intraocular lens. In all cases, the coma of the cornea is substantial, and it is highly desirable to use the cornea of the intraocular lens itself to offset the coma of the cornea, so that the resulting cascaded optical system has reduced coma.

Note that the values along the y-axis are not the values of $W_{131}$, but are the equivalent Seidel third-order aberration coefficients as reported by Oslo (using an entrance beam radius of 4 mm and a field angle of 15 degrees). The values themselves are less important than the shape factor at which these curves approach a minimum absolute value of coma. In other words, we want to know the shape factor X that minimizes coma for each of the IOL powers between 5 D and 30 D, shown in FIGS. 15-20. This preferred shape factor may be read from the graphs themselves, by selecting an X value that brings the third-order coma closest to zero.

These preferred shape factors are obtained from FIGS. 15-20 as follows: for 5 D X should be between −3 and −2.2, for 10 D X should be between −1.9 and −1.5, for 15 D X should be between −1.3 and −1.1, for 20 D X should be between −1.0 and −0.8, for 25 D X should be between −0.8 and −0.7, and for 30 D X should be between −0.6 and −0.5. These preferred shape factors describe the base radii of curvature of the intraocular lens that best offsets the coma of the cornea. When implanted in an eye with cornea that has a particular amount of coma, the intraocular lens with the preferred shape factor X optimally reduces the total amount of coma of the image at the retina. Note that the preferred shape factor only describes the base radii of curvature; the actual surfaces in the intraocular lens may also have additional aspheric or conic terms, in addition to its base radii. The preferred X ranges above depend somewhat on the lens thickness, and can be recalculated for any particular thickness.

Note that for intraocular lens powers less than about 20 D, the optimal shape of the lens is meniscus, with the concave surfaces facing away from the retina (i.e., for both lens surfaces, the center is closer to the retina than the edge is.) For powers greater than about 20 D, the optimal shape is bi-convex, with the more steeply curved surface facing the retina. There is a power or a range of powers between about 15 D and about 20 D where the optimal shape is plano-convex, with the flat side facing away from the retina.

Figure 21:
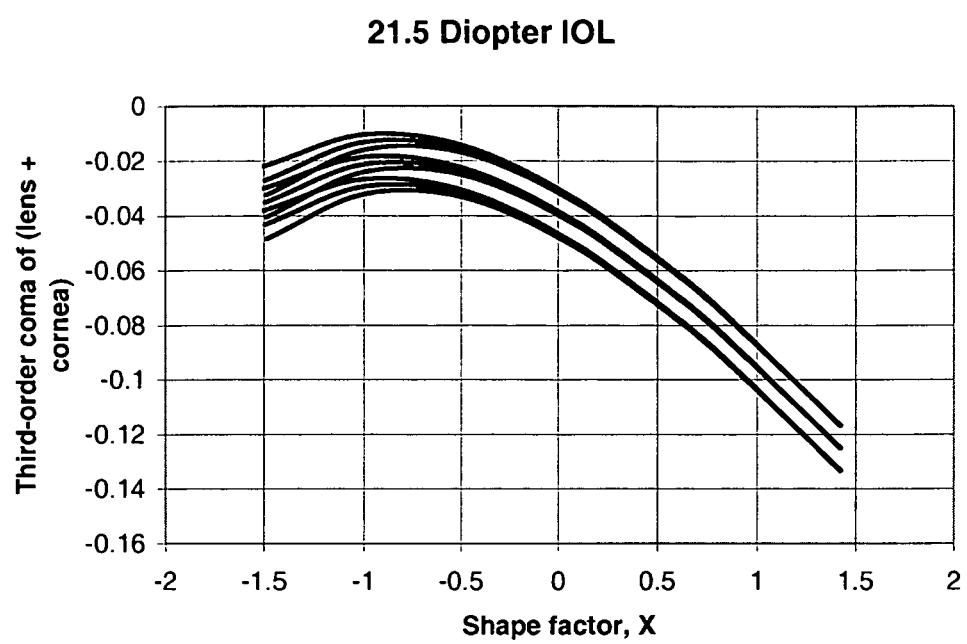
FIG. 21 is a graph of the third-order coma versus shape factor X, for various lens thicknesses and various cornea conic constants.

For the graphs of FIGS. 15-20, the thickness of the intraocular lens is set at 1.1 mm, and the conic constant of the cornea is set at −0.1. In real lenses and real patients, these values may vary, and it is instructive to show the effects of these variations on the preferred shape factor, X. FIG. 21 shows that they may vary over a reasonable range without substantially affecting the values of third-order coma, or without substantially changing the conclusions of FIGS. 15-20.

A set of nominal conditions is chosen, with a cornea radius of 7.704 mm and an axial length of 23.45, and a 21.5 D lens that is varied over shape factor X from about −1.5 to about 1.5. The analysis is repeated for a lens thickness of 1.0 mm, 1.1 mm and 1.2 mm, and for a conic constant of 0, −0.1 and −0.2, yielding the nine curves shown in FIG. 21. A bundling of the curves is seen at the rightmost edge of the plot, where the top bundle of curves has a conic constant of zero, the middle bundle has a conic constant of −0.1, and the bottom bundle has a conic constant of −0.2. This shows that altering the conic constant of the cornea produces an offset in the coma value that is independent of the shape factor of the IOL; this is merely a vertical translation of the curves. This also shows that small deviations in the measured values of cornea conic constant do not significantly affect the preferred shape factor (X~−0.9 to −0.8) for this particular power (21.5 D).

Included in each of the bundles at the rightmost edge of the plot in FIG. 21 is a plot for each of the lens thicknesses; these are indistinguishable for positive values of X, and separate slightly for negative values of X. This shows that altering the lens thickness has no significant effect on the preferred shape factor for this particular power. As a result, the actual thickness of the lens may be tailored to suit optical or non-optical needs. For instance, the lens may have a minimum thickness at its edge imposed by a particular grinding, polishing, or molding step in the manufacturing process. Or, the lens may have particular rigidity requirements. These thickness constraints based on manufacturing processes are well-known to one of ordinary skill in the art. The above modeling steps are shown for a center thickness of 1.1 mm, but apply equally well to other lens thicknesses.

Figure 22:
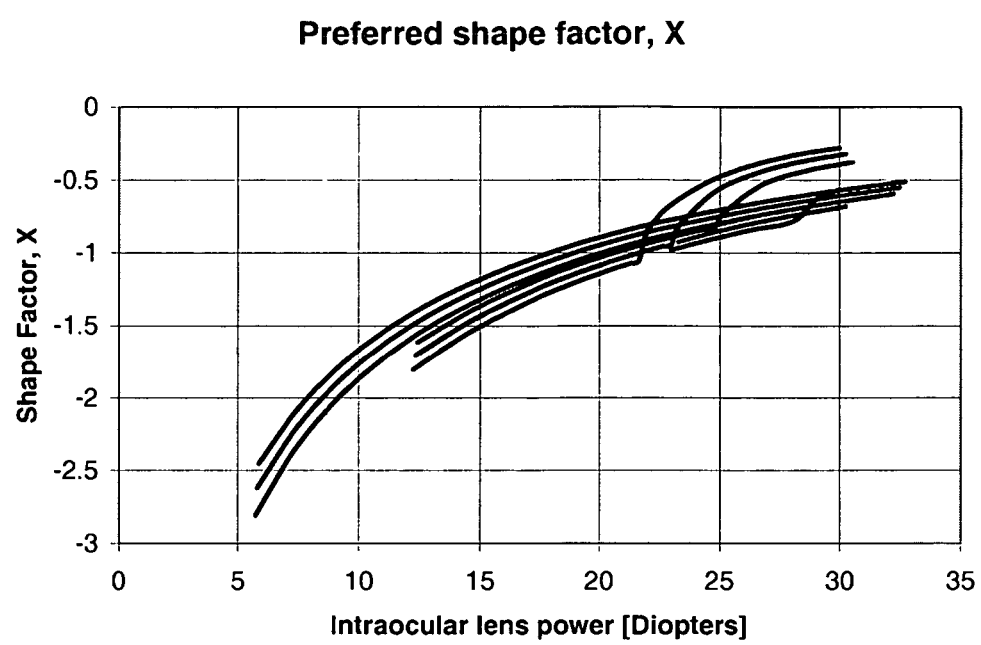
FIG. 22 is a graph of the preferred shape factor X versus the required intraocular lens power.

The results of the plots of FIGS. 15-20 may be summarized in FIG. 22, which shows the preferred shape factor X as a function of intraocular lens power. The values of X may be obtained in Oslo from the radii of the lens after optimization, where now both radii are set as variables, and an additional operand of "CMA3" is used, in addition to "PY". Alternately, the X values may be obtained directly from the paraxial spreadsheet, when the anterior radius is varied to set the total third-order coma as close to zero as possible. The only significant difference between the two calculation methods is that Oslo can use non-zero conic constants for its cornea, whereas the paraxial spreadsheet only works for purely spherical corneas.

The curves are obtained for two discrete values of cornea radius: 7 mm and 9 mm. In practice, the actual cornea radius for any given patient is highly likely to lie within this range, so the curves for 7 mm and 9 mm typically represent the extreme values for shape factor X. The three curves extending to the lower left corner of the graph are for a radius of 7 mm; the three just beneath them, beginning at roughly 12 D, are for 9 mm. Within each group of three curves, the top is for a lens thickness of 1.2 mm, the middle is for a lens thickness of 1.1 mm, and the bottom is for a lens thickness of 1.0 mm. To generate the curves themselves, the axial length is incremented, the radii are optimized to minimize coma, then the optimized radii values are used to calculate the shape factor X.

For the 7 mm radius (uppermost group of three curves), the trend is clear. For lens powers of less than about 17 D, the preferred shape factor is less than 1, resulting in a meniscus lens with the convex surface facing the retina and the concave surface facing away from the retina. For lens powers between about 17 D and about 20 D, the preferred shape is plano-convex, with the convex side facing the retina. For lens powers greater than about 20 D, the preferred shape is bi-convex, with the most steeply curved side facing the retina. By shaping the base radii according to X as in FIG. 22, the third-order coma of the eye is minimized, resulting in potentially more relaxed manufacturing and alignment tolerances, and better off-axis performance of the lens.

Furthermore, the R=7 mm group of curves is essentially independent of conic constant. Indeed, the values of preferred shape factor X are plotted for conic constants of 0 and −0.2, and the resulting curves lie entirely on top of one another. This conic independence is easily explained: the coma generated by the cornea is larger than any value of coma that the lens can generate. Therefore, the best that the lens can do is generate its maximum value of coma (of the opposite sign as the cornea's coma), to try and push the total value of coma back towards zero. This maximum value of lens coma occurs at a particular X value, which is the value reported on the graph. If the conic constant of the cornea varies between 0 and −0.2, resulting in a little more or a little less coma in the total system, the optimal X value remains unchanged, because the optimal X still generates the maximum lens coma (of the opposite sign as the cornea) to move the total system coma back toward zero.

For the R=9 mm curves, an interesting phenomenon occurs. For values of lens power less than about 21 D, the curves are also largely independent of conic constant. But for higher-power lenses, some of the curves show a branching effect, with the branches extending upward and to the right in the plots. Each of these branches is for a conic constant of 0, while the un-branched curves are for a conic constant of −0.2. The branched and unbranched curves coincide for lens powers lens than about 21 D.

The branching phenomenon is easily explained. For sufficiently high lens powers, the lens can generate a sufficient amount of third-order coma to completely offset that of the cornea. When this occurs, the total amount of third-order coma in the optical system is not merely minimized, as is the case for the R=7 mm curves, but it is truly cancelled by the lens in combination with the cornea. This shows up for R=9 mm because the less steeply-curved cornea itself generates less coma than for R=7 mm, and now falls within the range of possible coma values that can be truly cancelled by the lens, rather than just partially offset or minimized. This is also seen in FIGS. 15-20, in which the topmost curves (R=9 mm) for 25 D and 30 D actually cross zero coma. At the other radii (R=7 or 8 mm), the coma of the cornea is too large to be completely cancelled by the lens.

The branching and its dependence on conic constant is also easily explained. Given two cornea with the same base radius, the cornea having a conic constant of −0.2 has more third-order coma than one having a conic constant of 0. The greater the departure from zero, the higher the coma. For the upper branches of the curves, all have a conic constant of 0, which means that the third-order coma of the cornea is small enough that it can be completely cancelled by the coma of the lens. For the lower branches of the curves, all have a conic constant of −0.2, which increases the coma of the cornea enough so that it cannot be completely offset by that of the lens; it can be merely reduced by the lens.

In practice, for a typical set of cornea conditions, such as those in FIG. 21, the cornea generally has more third-order coma than the lens, regardless of choice of shape factor X. When this occurs, the best one can do is choose a shape factor X so that the lens generates the most amount of coma of an opposite sign of that of the cornea, to best offset the third-order coma of the cornea and reduce the total amount of coma in the eye system.

Some values and preferred ranges may be read from FIGS. 15-22. For powers between 0 diopters and 10 diopters, the preferred shape factor is between −3 and −1.6. For powers between 5 diopters and 15 diopters, the preferred shape factor is between −3 and −1.2. For powers between 10 diopters and 20 diopters, the preferred shape factor is between −1.9 and −0.8. For powers between 15 diopters and 25 diopters, the preferred shape factor is between −1.5 and −0.5. For powers between 20 diopters and 30 diopters, the preferred shape factor is between −1.2 and −0.2. For powers greater than 30 diopters, the preferred shape factor is between −0.7 and 0. It will be understood by one of ordinary skill in the art that these preferred shape factor ranges depend on the refractive index of the lens material. For these numerical examples, a refractive index of 1.4577 is used. If a different material is used for the lens, the lens will have a different refractive index, and the curves of FIGS. 15-22 will shift accordingly, thereby producing a different lens shape than those described herein. Note that the methodology of designing the lens remains the same, regardless of the choice of material or its refractive index.

Note that the above optimization step does not produce a completed lens. Instead, the optimization adjusts only the base radius of curvature of the posterior lens so that the paraxial focus falls on the retina. In order to complete the design, with sufficiently reduced aberrations on- and off-axis, one or more aspheric terms should be added to one or both of the lens surfaces. Optionally, a conic constant may also be added to one or both of the lens surfaces.

It should be mentioned that although X is derived to describe only infinitely thin lenses, the lenses used here are sufficiently thin so that X still provides a meaningful description of the lens shape. Note also that because the incident and exiting media have the same refractive index, X is simply expressed in terms of the radii of curvature of the anterior and posterior lens surfaces, as follows:

$$X = (R_{posterior} + R_{anterior})/(R_{posterior} - R_{anterior})$$

Note also that if the paraxial raytracing spreadsheet of FIG. 14 is used to calculate the optimal shape factor X, the resulting value of X is independent of both the entrance pupil diameter (or, equivalently, the incident marginal ray height) and the field of view (or, equivalently, the incident chief ray angle). This arises from the scalability of a paraxial raytrace, and is a particularly pleasing aspect of the paraxial spreadsheet.

It is instructive to summarize the findings thus far. First, for a set of measured patient conditions (cornea radius and axial length) or a set of assumed conditions (corneal radius or radii, axial length and anterior chamber depth), and a set of conventions or assumptions (effective lens position, vertex distance, desired spectacle power, refractive indices), an algebraic expression based on thin lens optics may be used to predict the required intraocular lens power. Second, once the intraocular lens power is known, a range of preferred shape factors may be found, which determine the base (i.e., spherical) radii of the two lens surfaces. The preferred shape factor adjusts the third-order coma of the lens to largely offset the coma of the cornea, so that the image at the retina has a reduced amount of third-order coma. This reduced-coma condition provides more relaxed manufacturing and alignment tolerances for the lens, and improved off-axis image quality. Furthermore, the preferred shape factor is largely independent of both lens thickness and the conic constant of the cornea.

Once a preferred shape factor X is determined, the base radii R of the anterior and posterior surfaces are found by $$R_{anterior} = 2(n_{lens} - n_{eye})/[\phi(X-1)],$$

$$R_{posterior} = 2(n_{lens} - n_{eye})/[\phi(X+1)],$$

where $\phi$ is the power of the intraocular lens, $n_{lens}$ is the refractive index of the lens (typically 1.4577), and $n_{eye}$ is the refractive index of the eye (typically 1.336).

Note that the refractive index on one side of the lens may differ from the refractive index on the opposite side of the lens. In this case, the numerical values of $n_{eye}$ in the two above equations may be replaced by the incident refractive index in the anterior equation, and the exiting refractive index in the posterior equation.

Note that other suitable materials may be used, which may have refractive indices that differ from the example of 1.4577 used here. For different materials, the same design process is followed, only with the proper value of refractive index entered in the appropriate cell in the spreadsheet of FIG. 14. A complete analysis shows that the preferred shape factor X depends implicitly on refractive index, and that the curves shown in FIG. 22 will vary depending on the choice of lens material. It is understood by one of ordinary skill in the art that the design methodology remains the same for each choice of lens material, although the precise shape factor X for each lens power varies.

Note that these methods may be applied to a condition associated with an individual patient, an average patient, or a special group of patients. One such group could be a group of patients having undergone refractive surgery, such as PRK, LASEK, LASIK or RK. Another group could be a group of patients having undergone corneal surgery, such as those suffering from special ocular conditions such as kerataconous or corneal disease. Note also that the intraocular lens could be monofocal, bifocal, multifocal, or a phakic lens. If the IOL is a phakic lens, then the natural lens of the eye should be included in the calculations outlined here. In addition, the methods described herein may also be applied to individual cornea data taken from corneal topography, i.e., corneas where the individual amount of corneal spherical aberration is known. Alternatively, the methods may be applied to a model cornea that reflects average measurements for a "normal" or "special" group of patients.

Once the base radii of curvature of the lens are determined, the next step in the design is the addition of aspheric terms or a conic constant to one or both of the surfaces in the lens, so that on-axis aberrations are reduced. This process is detailed in the next section.

Optimizing an Intraocular Lens Design

This section describes how to add conic and/or aspheric terms to one or both of the surfaces of the intraocular lens. For the purposes of this document, a conic constant is considered to be an aspheric term.

By choosing the base radii of curvature of the lens as described in the previous section, the third-order coma of the system is minimized or reduced, ensuring that the off-axis performance of the lens is roughly the same as its on-axis performance. However, the lens should also have reduced spherical aberration, which improves both on-axis and off-axis performance. A preferred way of reducing spherical aberration is to introduce a conic constant and/or one or more aspheric terms to one or more of the surfaces on the intraocular lens. Note that adjusting the base radii of curvature affects the spherical aberration, but also affects the coma at the same time. It is preferred to first fix the coma by selecting the base radii according to the above steps, then afterwards correct the remaining spherical aberration by adding a conic constant and/or aspheric terms on one or both of the intraocular lens surfaces.

A convenient way to prepare and finalize any design is with a raytracing program. These raytracing programs are relatively common, and some commercially available examples include ZEMAX, Oslo, Code V, and others. Using a raytracing program, any of the parameters of the intraocular lens may be optimized and/or toleranced. These optimizations may preferably use the base radii obtained from the preferred shape factor as a starting point, but may depart somewhat from it during the optimization process.

For a given patient, a practitioner typically measures the base radius of curvature of the cornea (or radii of curvature of both the anterior and posterior cornea) and the axial length of the eye. From the algebraic formula provided above, or by any other suitable method, the practitioner determines a required power value for the intraocular lens. As described earlier, FIG. 12 shows the relationship between cornea radius, axial length, and the required power of the IOL. For any given power, there are many combinations of cornea radius and axial length that will require said power. For instance, a patient with an axial length of 24 mm and a cornea radius of 7.8 mm, and a patient with an axial length of 25 mm and a cornea radius of 8.3 mm both require an IOL power 20 diopters. Given this multiplicity, which set of conditions does one use when designing the lens itself?

A reasonable assumption is that one should use an "average" radius and conic constant for the cornea, and vary the axial length to achieve the particular desired power. The "average" cornea values of radius and conic constant are chosen to be 7.5 mm and −0.1, respectively. The values of axial length are then determined from FIG. 12 to yield the appropriate value of IOL power. On average, a lens designed in this manner generally performs well when used with other radius/axial length combinations that also require the same IOL power. In other words, the IOL is designed for a statistically "average" cornea.

There are a number of averaging schemes that may be used for measurements taken on a particular population. For instance, if the radius and conic constant are measured for a group of patients, then two exemplary ways to determine the average coma are detailed below. In one scheme, the radius measurements are averaged to form an average radius, and the conic constant measurements are averaged to form an average conic constant. Then, the average radius and average conic constant are plugged into a model of the eye to determine an average coma. In the second scheme, a value of coma is first determined for each patient in the population, then the coma values themselves are averaged to form an average coma. These two schemes are merely exemplary, and other appropriate averaging schemes may also be used.

Alternatively, if more sophisticated measurements are made on the patient's cornea than just the corneal radius and axial length, it may be possible to quantify more than just the required optical power. For instance, if the actual coma of the cornea is measured or inferred from measurements, it may be possible to tailor a design or a family of designs to accommodate specific values of coma. Consider an analogy of shoe widths, where each shoe is available in a particular size, but may be specified in terms of "wide" or "narrow". Analogously, each lens may be made available in not just a power, but in a "high coma" or "low coma" condition.

During optimization, the various parameters of the intraocular lens are fleshed out. The following steps are exemplary, and show how a lens may be designed for a particular power. It will be appreciated that other design steps may be used, in addition to or in place of the following steps.

The lens is designed for a particular power, so optical power is the primary input constraint. Recall that typically, two quantities are measured for each patient: axial length, and radius of the cornea. From these two quantities, a formula based on thin-lens calculations determines a required optical power for the intraocular lens. There are many combinations of axial length and corneal radius that produce the same required optical power, so we arbitrarily choose an average cornea radius and conic constant, and design for this particular average cornea, but with varying axial lengths to account for the range of required powers. Typically, a manufacturer of intraocular lenses provides off-the-shelf lenses in power increments of 0.5 D, usually in the range of 5 D to 30 D. Naturally, the power range or increments can vary from these values. Alternatively, the power determination may be based on measurements from a number of eyes, using an average cornea and an average axial length.

It is preferable to choose a lens thickness fairly early in the design stage, although the thickness may be varied at any step in the design process. Common thicknesses are in the range of 1.0 mm to 1.2 mm, although they may also vary outside this range. The thickness is commonly chosen for non-optical reasons, such as for lens rigidity, or a particular edge thickness constraint, or a particular mechanical constraint that arises from a manufacturing process. For the exemplary design detailed below, a thickness of 1.1 mm is chosen.

Given the lens power and lens thickness, the next two quantities to be determined are the radii of curvature of the anterior and posterior lens surfaces. As discussed in previous sections, these two curvatures are chosen to (1) determine the power of the lens, and (2) minimize the third-order coma in the full optical system. Spherical aberration is addressed in a later design step, but not at this point. Recall that the two radii of curvature may be equivalently expressed as values of lens power $\phi$ and lens shape factor X. For a given power, there is a preferred shape factor that minimizes the third-order coma in the system, as shown graphically in FIG. 22. One may read the values off the graph in FIG. 22, then convert $\phi$ and X back to radii for the front and rear surfaces via formulas provided above.

Alternatively, one may use the spreadsheet of FIG. 14 to directly generate the values of the radii. Most conveniently, the user may define a cell as a "merit function" to be minimized. The value of the merit function cell is defined by the user, and may, for example, equal ((Actual power−Desired power)$^2$+(Total W131)$^2$), or any other appropriate value. The spreadsheet can then use a solver to minimize the merit function cell, or set it as close as possible to zero, by changing the values of the "axial length" and "anterior lens curvature" cells. The power term in the merit function may optionally be weighted, such as by a factor of 10000 or some other appropriate weighting term. Once the solver converges, the values of the anterior and posterior radii may be read directly from the spreadsheet, along with the shape factor X and axial length, if desired. Note that the spreadsheet of FIG. 14 does not accommodate a non-zero conic constant.

As a third alternative, a raytracing program may be used to generate the two radii directly. For instance, in Oslo, once the basic system is entered and the surface-to-surface spacings are all properly set, the two radii of the lens may be set as variables, and two aberration operands may be set: PY, which sets the axial ray height at the retina as close to zero as possible, and CMA3, which ensures that the third-order coma of the whole system is brought as close as possible to zero. During this step, it is preferable to stop down the lens to a smaller entrance beam radius (say, 1 mm), and a reduced field angle (say, 1 degree), so that the lens performance is dominated by third-order spherical aberration on- and off-axis, and third-order coma off-axis, without the complications of other aberrations in the system. The radii produced by this step do not directly depend on the choice of entrance beam radius or field angle.

It is found that for the "average" cornea radius of 7.5 mm, the lens radius values produced by either the spreadsheet or the raytracing program are essentially independent of conic constant value, for values in the range of −0.2 to 0. As discussed in a previous section, the optimal shape factor X for the lens (or, equivalently, the optimal base radii for the lens surfaces), helps offset the coma of the cornea, but generally does not completely cancel it. Put another way, the cornea (with R=7.5 mm) has more third-order coma than the lens (with spherical surfaces at this design step), regardless of X, so that the best the lens can do is choose an X to generate the maximum amount of coma of the opposite sign as the cornea, to attempt to bring the total amount of coma back toward zero.

Stated again, the base radii of curvature of the front and back surfaces of the lens are preferably chosen to minimize the third-order coma of the whole system. Note that because the lens thickness is fixed, the shape factor X is generally the only quantity that substantially affects the off-axis performance of the lens. Although aspheric and/or conic terms may be added to one or both of the lens surfaces, these primarily improve lens performance on-axis by reducing spherical aberration. Off-axis performance is dominated by third-order coma, and third-order coma is best reduced by adjusting the shape factor X of the lens.

Once the base radii of curvature of the front and rear surfaces are determined, thereby ensuring good off-axis performance, the on-axis performance may be improved by adding a conic and/or aspheric terms to one or both lens surfaces. These terms reduce spherical aberration, which affects both on-axis and off-axis performance of the lens.

Although the conic and/or aspheric terms may be added to both lens surfaces, it is found that having them on only one of the surfaces works adequately. Preferably, these conic and/or aspheres are present on the surface facing the retina, which for these designs typically is more steeply curved and contains the majority of the optical power of the lens. The surface facing away from the retina may be left purely spherical, i.e., devoid of conic and/or aspheric terms or components. Alternatively, the aspheric terms can be placed on either or both of the anterior and posterior surfaces.

It is found that the conic constant ("CC" in Oslo) is largely redundant with the aspheric terms, and may be omitted (i.e., left equal to zero). This may be understood by examining the aspheric terms themselves, and noting which aberrations they correct. A fourth-order aspheric term ("AD" in Oslo) may be used to correct for third-order spherical aberration (expressed mathematically as "$W_{040}$"). A sixth-order aspheric term ("AE" in Oslo) may be used to correct for fifth-order spherical aberration ("$W_{060}$"). Likewise, an eighth-order aspheric term ("AF" in Oslo) may be used to correct for seventh-order spherical aberration ("$W_{080}$"). There are higher-order aspheric terms available, but they are generally not needed. Note that the order of each aspheric term corresponds nicely to the order of spherical aberration that it corrects. For example, if a design shows an unusual amount of fifth-order spherical aberration, it may often be corrected by adjusting the AE term of one of the lens surfaces, without affecting the third-order spherical aberration components. In contrast, adjusting the conic constant of a surface affects essentially all the orders of spherical aberration, including the fourth, sixth, eighth, and higher orders. Adjusting a CC term to correct for $W_{040}$ is possible, but it often still requires use of AE, AF, and higher-order aspheric terms. In particular, use of both CC and AD to correct for $W_{040}$ is largely unnecessary. Therefore, we choose that the conic constant of these lens designs remains zero, although it may also be used for optimizing on-axis performance.

Adding the aspheric terms to the second (i.e., posterior) lens surface is preferably done using a commercially-available lens design or raytracing program, such as Oslo, ZEMAX, Code V, and others. One approach is to set the field of view to zero (because we wish to optimize on-axis performance in this step), set the aspheric terms AD, AE and AF as variables, and optimize using on-axis spot size or on-axis wavefront error in the merit function. This approach works adequately, and produces functional values for AD, AE and AF. This approach is also fast, providing values in essentially one optimization step. Because the base radii are not set as variables, the thickness between the lens and the retina may also be set as a variable and optimized along with the other terms during this step. Alternatively, the specific values of $3^{rd}$ order, $5^{th}$ order, and $7^{th}$ order spherical aberration may all be set to zero, but this may leave some residual $9^{th}$ order spherical aberration in addition to even higher orders.

A more insightful approach is detailed as follows. This approach adds one aspheric term at a time, which corrects for one order of spherical aberration at a time. It is worthwhile to try this approach at least once, so that the designer may better understand when and why certain aspheric terms are necessary, and better understand the limitations of on- and off-axis performance of the finished lens.

We assume at this stage that the lens is entered into the raytracing program of choice, that the front and rear radii of the lens are determined (from a pervious step), and that the lens is stopped down beyond its design criteria. For instance, the entrance beam radius is stopped down to 1 mm, and the field of view is stopped down to 1 degree.

As an optional check, we can ensure that the paraxial image plane is truly coincident with the retina. We set as a variable either the radius of the second lens or the thickness between the lens and the retina. We set an appropriate merit function; in Oslo, "PY" can be used as the sole aberration operand. We then optimize. The designer should find that the radius or thickness changed by an extremely small amount. If the values are initially transferred from the spreadsheet with four significant figures, then they should remain unchanged after optimization to four significant figures. The radius or thickness is then removed as a variable, completing this optional check of the image plane.

With the lens in its stopped-down state, the dominant wavefront aberration should be third-order spherical aberration, or $W_{040}$. This is brought under control by adding a fourth-order aspheric term AD to the posterior surface of the lens. We set AD on this surface (surface 5 in the schematic of FIG. 13) as the sole variable. We add the aberration operand "SA3" to the merit function, ensuring that the third-order spherical aberration of the system is minimized. We then optimize. The value of AD should now be set to a particular non-zero value. The on-axis performance of the lens should be superb, with a Strehl Ratio close to one, such as 0.999. Off-axis, the lens should show an insignificant amount of coma, such as roughly 0.02 waves or less.

Next, we control fifth-order spherical aberration by adding a sixth-order aspheric term AE to the posterior lens surface. We open the pupil diameter to about 2 mm so that we can see some fifth-order spherical aberration. We add AE on surface 5 as a variable, and add the aberration operand "SA5" to the merit function. We then optimize. The value of AE should now be set to a particular non-zero value. In addition, the value of AD should remain essentially unchanged, even if it remained as a variable during this step, which shows the correspondence between AD and third-order spherical aberration. There should again be superb on-axis performance, with a Strehl Ratio of 0.999 or higher. Off-axis, there should still be a negligibly small amount of coma.

Finally, we control seventh-order spherical aberration by adding a eighth-order aspheric term AF to the posterior lens surface. We open the pupil diameter to about 3 mm so that we can see some seventh-order spherical aberration. We add AF on surface 5 as a variable, and add the aberration operand "SA7" to the merit function. We then optimize. The value of AF should now be set to a particular non-zero value. In addition, the values of AD and AE should also remain essentially unchanged. Performance on-axis should be good, although not as superb as in the previous two optimization steps. Off-axis, there should still be a negligibly small amount of coma.

After these three optimization steps, values of AD, AE and AF are obtained. These values may be fine-tuned by changing the merit function from one that minimizes individual aberrations to one that minimizes spot size or wavefront aberration. We keep AD, AE and AF as variables, set the field angle to essentially zero, then optimize. After optimization, we see that the value of AD remained largely unchanged, the value of AE may have changed by a small amount, say 10%, and AF may have changed by a substantial amount, such as a factor of three or more. The resulting performance of the lens on-axis should again be superb, with a Strehl Ratio of essentially 1.0. Analysis of the wavefront error after this spot size optimization shows an extremely small amount of some high-order spherical aberration, with magnitudes of about 0.002 waves or less.

It should be noted that once the base radii of curvature are determined from the early design step, they should preferably not be further optimized in tandem. For instance, both radii should not be set as variables during any of the subsequent optimization steps, such as the elimination of third-order spherical aberration. The shape factor X also influences the amount of spherical aberration in the lens, but because spherical aberration can be corrected by the addition of aspheric terms, we use X to instead correct for coma, which is not easily influenced by aspheric coefficients.

In practicality, although the step-by-step optimization process is informative for the designer, it may be skipped altogether by setting AD, AE and AF of the back lens surface as variables, setting the field angle to essentially zero, opening the entrance pupil radius to 3 mm or 4 mm (or any other suitable value), and optimizing for minimum spot size or minimum wavefront error. Along with the refractive index (1.4577 in these examples), thickness (1.1 mm in this example), and radii of curvature (determined by the previous section to minimize coma and thereby maximize off-axis performance), the aspheric terms AD, AE and AF of one of the lens surfaces thus complete the lens design.

Note that although the aspheric terms are applied to the back surface of the lens, they may just as easily be applied to the front surface, applied to both, or divided between the two. Switching the aspheric terms from one surface to the other has little effect on the overall lens performance. There may be some advantage to making one particular side of the lens aspheric, such as commonality of a surface profile among various designs, say if a particular mold is to be shared among the designs.

This design process may be repeated as often as required for different powers, so that a complete line of off-the-shelf lenses may accommodate the full range of patients. A typical range of required powers is 5 D to 30 D. A typical power increment between available lenses may be 0.5 D, although 0.25 D or another suitable increment may be used.

Sample Designs

Each of the designs shown in this section is designed in the same manner, as follows. For a given power, the spreadsheet of FIG. 14 is used to find the "optimal" or "preferred" starting point, with an X value that minimizes the third-order coma of the full optical system. In addition to X, the spreadsheet provides, equivalently, the radii of the front and rear surfaces of the lens, as well as the appropriate surface-to-surface spacings. All of these starting points are then optimized in Oslo. The aspheric terms AD, AE and AF are added to the second surface of the lens using a merit function that minimizes the RMS spot size, and performing the optimization at an entrance pupil radius of 3 mm and zero field angle. All the lenses are 1.1 mm thick, with a refractive index of 1.4577, and are designed for a cornea with a radius of 7.5 mm and a conic constant of −0.15. This cornea is intended to represent an "average" cornea.

Figure 23:
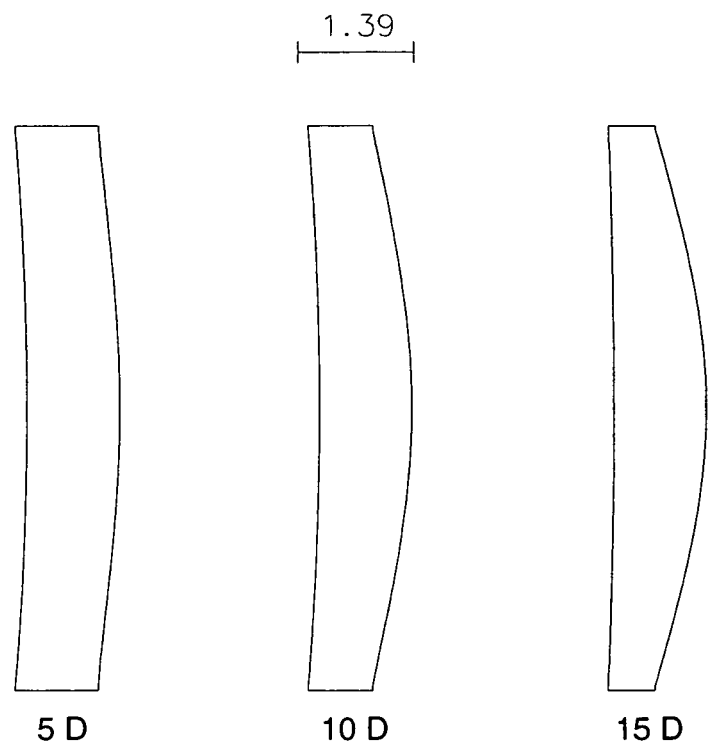
FIG. 23 is a plan drawing of completed lens designs for optical powers of 5 D, 10 D and 15 D.
Figure 24:
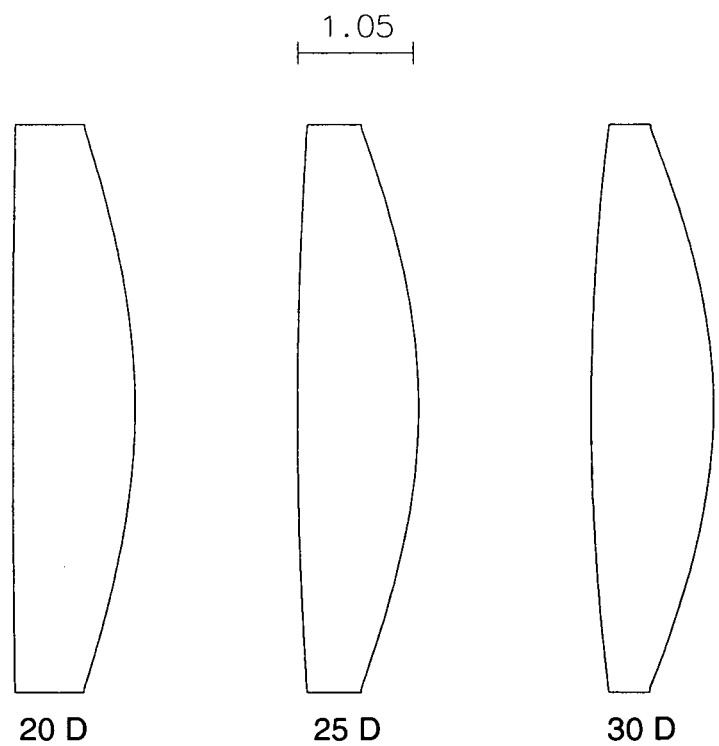
FIG. 24 is a plan drawing of completed lens designs for optical powers of 20 D, 25 D and 30 D.

Six sample designs are carried to completion, and are shown in FIGS. 23 and 24. The designs of FIG. 23, which are for powers of 5, 10 and 15 diopters, are drawn with a part diameter of 8 mm. The designs of FIG. 24, which are for powers of 20, 25 and 30 mm, are drawn with a part diameter of 6 mm. In practice, the actual thickness of the part may be altered to accommodate any non-optical concerns, like a minimum edge thickness, for example. For consistency, each of these designs uses a center thickness of 1.1 mm, although any suitable thickness may be used.

The 5 D lens has a shape factor X of −2.23, an anterior radius of −39.74 mm, and a posterior radius of −15.13 mm. The posterior surface has three aspheric terms: AD=1.014×$10^{-3}$ mm$^{-3}$, AE=−4.933×$10^{-6}$ mm$^{-5}$, and AF=1.157×$10^{-7}$ mm$^{-7}$. The distance between the lens and the retina is 22.03 mm.

The 10 D lens has a shape factor X of −1.58, an anterior radius of −41.85 mm, and a posterior radius of −9.449 mm. The posterior surface has three aspheric terms: AD=1.333×$10^{-3}$ mm$^{-3}$, AE=−1.067×$10^{-5}$ mm$^{-5}$, and AF=1.988×$10^{-7}$ mm$^{-7}$. The distance between the lens and the retina is 20.36 mm.

The 15 D lens has a shape factor X of −1.19, an anterior radius of −86.72 mm, and a posterior radius of −7.427 mm. The posterior surface has three aspheric terms: AD=1.741×$10^{-3}$ mm$^{-3}$, AE=−1.624×$10^{-5}$ mm$^{-5}$, and AF=3.616×$10^{-7}$ mm$^{-7}$. The distance between the lens and the retina is 18.88 mm.

The 20 D lens has a shape factor X of −0.93, an anterior radius of 170.5 mm, and a posterior radius of −6.307 mm. The posterior surface has three aspheric terms: AD=2.211×$10^{-3}$ mm$^{-3}$, AE=−2.215×$10^{-5}$ mm$^{-5}$, and AF=6.479×$10^{-7}$ mm$^{-7}$. The distance between the lens and the retina is 17.58 mm.

The 25 D lens has a shape factor X of −0.75, an anterior radius of 39.01 mm, and a posterior radius of −5.549 mm. The posterior surface has three aspheric terms: AD=2.750×$10^{-3}$ mm$^{-3}$, AE=−2.849×$10^{-5}$ mm$^{-5}$, and AF=1.136×$10^{-6}$ mm$^{-7}$. The distance between the lens and the retina is 16.45 mm.

The 30 D lens has a shape factor X of −0.62, an anterior radius of 21.47 mm, and a posterior radius of −4.980 mm. The posterior surface has three aspheric terms: AD=3.373×$10^{-3}$ mm$^{-3}$, AE=−3.557×$10^{-5}$ mm$^{-5}$, and AF=1.985×$10^{-6}$ mm$^{-7}$. The distance between the lens and the retina is 15.44 mm.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. An intraocular lens having an optical power and a shape factor for implantation in an eye of a patient in which the natural lens has been removed, the eye having a cornea, a retina, and an axial length defined by a distance between the cornea and the retina, the cornea having a radius of curvature and a coma, the coma having a sign, comprising:

an anterior surface having an anterior radius, Ra;
a posterior surface having a posterior radius, Rp; and
an aspheric surface on at least one of the anterior surface and the posterior surface, wherein the aspheric surface reduces spherical aberration of the cornea;
wherein the anterior radius and the posterior radius determine the optical power and the shape factor;
wherein the shape factor is negative, with a lower limit of about −3;
wherein the intraocular lens has a coma based on the shape factor, the intraocular lens coma having a sign opposite to the sign of the cornea coma; and
wherein the optical power of the intraocular lens is between 0 diopters and 30 diopters selected from the group consisting of 5 diopters, 10 diopters, 15 diopters, 20 diopters, 25 diopters, and 30 diopters;
wherein the intraocular lens with an optical power of 5 diopters has a shape factor between about −3 and about −2.2;
wherein the intraocular lens with an optical power of 10 diopters has a shape factor between about −1.9 and −1.5;
wherein the intraocular lens with an optical power of 15 diopters has a shape factor between about −1.3 and −1.1;
wherein the intraocular lens with an optical power of 20 diopters has a shape factor between about −1.0 and −0.8;
wherein the intraocular lens with an optical power of 25 diopters has a shape factor between about −0.8 and −0.7;
wherein the intraocular lens with an optical power of 30 diopters has a shape factor between about −0.6 and −0.5; and
wherein the coma of the intraocular lens minimizes the coma of the cornea when light passes through both the cornea and the intraocular lens sequentially.

2. The intraocular lens of claim 1, wherein:
the lens has a refractive index, n;
the lens has an incident refractive index, ni;
the lens has an exiting refractive index, ne;
the lens has a thickness T; and
the optical power is determined by $$P=[(n-ni)/Ra]+[(ne-n)/Rp]-[T/n]\times[(n-ni)/Ra]\times[(ne-n)/Rp].$$

3. The intraocular lens of claim 1, wherein the intraocular lens with an optical power between 0 diopters and 10 diopters has a shape factor between about −3 and about −1.6.

4. The intraocular lens of claim 1, wherein the intraocular lens with an optical power between 5 diopters and 15 diopters has a shape factor between about −3 and about −1.2.

5. The intraocular lens of claim 1, wherein the optical power of the intraocular lens correlates to the axial length of the eye of the patient.

6. The intraocular lens of claim 1, wherein the optical power of the intraocular lens correlates to the radius of curvature of the cornea of the patient.

7. The intraocular lens of claim 1, wherein the optical power of the intraocular lens correlates to the axial length of the eye of the patient and the radius of curvature of the cornea of the patient.

8. The intraocular lens of claim 1, wherein wherein the shape factor of the intraocular lens correlates to the radius of curvature of the cornea of the patient.

9. The intraocular lens of claim 1, wherein the shape factor of the intraocular lens correlates to a power of the cornea of the patient.

10. The intraocular lens of claim 1, wherein the lens with an optical power between 10 diopters and 20 diopters has a shape factor between about −1.9 and about −0.8.

11. The intraocular lens of claim 1, wherein the lens with an optical power between 15 diopters and 25 diopters has a shape factor between about −1.5 and about −0.5.

12. The intraocular lens of claim 1, wherein the lens with an optical power between 20 diopters and 30 diopters has a shape factor between about −1.2 and about −0.2.

13. An intraocular lens having an optical power for implantation in an eye having a cornea, a retina, and an axial length defined by a distance between the cornea and the retina, the cornea having a radius of curvature and a coma, the intraocular lens comprising:

an anterior surface having an anterior radius, Ra;

a posterior surface having a posterior radius, Rp;

wherein the optical power, P, and a shape factor, X, are defined at least by the anterior radius and the posterior radius;

wherein the shape factor X is negative, with a lower limit of about −3;

wherein the intraocular lens has a coma based on the shape factor, the intraocular lens coma having a sign opposite to the sign of the cornea coma;

wherein the optical power P of the intraocular lens correlates to at least one of the axial length of the eye and the radius of curvature of the cornea and is between 0 diopters and 30 diopters selected from the group consisting of 5 diopters, 10 diopters, 15 diopters, 20 diopters, 25 diopters, and 30 diopters;

wherein the intraocular lens with an optical power of 5 diopters has a shape factor between about −3 and about −2.2;

wherein the intraocular lens with an optical power of 10 diopters has a shape factor between about −1.9 and −1.5;

wherein the intraocular lens with an optical power of 15 diopters has a shape factor between about −1.3 and −1.1;

wherein the intraocular lens with an optical power of 20 diopters has a shape factor between about −1.0 and −0.8;

wherein the intraocular lens with an optical power of 25 diopters has a shape factor between about −0.8 and −0.7;

wherein the intraocular lens with an optical power of 30 diopters has a shape factor between about −0.6 and −0.5;

wherein the intraocular lens coma minimizes the coma of the cornea when light passes through both the cornea and the intraocular lens sequentially;

wherein at least one of the surfaces is an aspheric surface; and wherein the aspheric surface reduces a spherical aberration of the cornea for the value of optical power.

14. The intraocular lens of claim 13, wherein the lens with an optical power between 0 diopters and 10 diopters has a shape factor between about −3 and about −1.6.

15. The intraocular lens of claim 13, wherein the lens with an optical power between 5 diopters and 15 diopters has a shape factor between about −3 and about −1.2.

16. The intraocular lens of claim 13, wherein the lens with an optical power between 10 diopters and 20 diopters has a shape factor between about −1.9 and about −0.8.

17. The intraocular lens of claim 13, wherein the lens with an optical power between 15 diopters and 25 diopters has a shape factor between about −1.5 and about −0.5.

18. The intraocular lens of claim 13, wherein the lens with an optical power between 20 diopters and 30 diopters has a shape factor between about −1.2 and about −0.2.

19. The intraocular lens of claim 13, wherein the shape factor is determined by:

$$x=(Rp+Ra)/(Rp-Ra).$$

20. The intraocular lens of claim 13, wherein:
the lens has a refractive index, n;
the lens has an incident refractive index, ni;
the lens has an exiting refractive index, ne;
the lens has a thickness T; and
the optical power is determined by $$P=[(n-ni)/Ra]+[(ne-n)/Rp]-[T/n]\times[(n-ni)/Ra]\times[(ne-n)/Rp].$$

21. The intraocular lens of claim 13, wherein the cornea coma has a sign, and the intraocular lens coma has a sign opposite to the sign of the cornea coma.

* * * * *